US012685546B2

(12) United States Patent
Goyal

(10) Patent No.: US 12,685,546 B2
(45) Date of Patent: Jul. 21, 2026

(54) CATHETER SYSTEMS ENABLING IMPROVED ASPIRATION FROM CEREBRAL ARTERIES

(71) Applicant: MG Stroke Analytics Inc., Calgary (CA)

(72) Inventor: Mayank Goyal, Calgary (CA)

(73) Assignee: MG Stroke Analytics Inc., Calgary (CA)

( * ) Notice: Subject to any disclaimer, the term of this patent is extended or adjusted under 35 U.S.C. 154(b) by 582 days.

(21) Appl. No.: 17/597,834

(22) PCT Filed: Jul. 24, 2020

(86) PCT No.: PCT/CA2020/051026
§ 371 (c)(1),
(2) Date: Jan. 25, 2022

(87) PCT Pub. No.: WO2021/012058
PCT Pub. Date: Jan. 28, 2021

(65) Prior Publication Data
US 2022/0273322 A1 Sep. 1, 2022

Related U.S. Application Data

(60) Provisional application No. 62/878,652, filed on Jul. 25, 2019, provisional application No. 63/029,401, filed on May 23, 2020.

(51) Int. Cl.
*A61B 17/22* (2006.01)
*A61F 7/12* (2006.01)
(Continued)

(52) U.S. Cl.
CPC .............. *A61B 17/22* (2013.01); *A61F 7/12* (2013.01); *A61M 1/75* (2021.05); *A61M 25/008* (2013.01);
(Continued)

(58) Field of Classification Search
CPC .......... A61B 17/22; A61B 2017/22038; A61B 2017/22079; A61B 2017/22082;
(Continued)

(56) References Cited

U.S. PATENT DOCUMENTS

| | | | | |
|---|---|---|---|---|
| 4,836,187 A | * | 6/1989 | Iwakoshi | A61M 13/003 |
| | | | | 600/157 |
| 5,423,772 A | * | 6/1995 | Lurie | A61N 1/056 |
| | | | | 600/374 |

(Continued)

FOREIGN PATENT DOCUMENTS

WO    WO2018/145212 A1    8/2018

OTHER PUBLICATIONS

WIPO, International Search Authority, International Search Report and Written Opinion mailed Oct. 29, 2020 in International Patent Application No. PCT/CA2020/051026, 18 pages.

(Continued)

*Primary Examiner* — Katherine H Schwiker
*Assistant Examiner* — Zehra Jaffri
(74) *Attorney, Agent, or Firm* — Inskeep IP Group, Inc.

(57) ABSTRACT

A distal entry point (DEP) to brain aspiration (D2BA) catheter for use in an endovascular procedure for gaining access to cervical and cerebral arteries in a brain of a patient and aspirating one or more intracranial clots from the cerebral arteries, comprising a soft distal tip region having a distal length sufficient to extend from a level 1 or level 2 arterial segment of a cerebral artery or equivalent to an upper neck arterial vessel, a stiffness enabling movement through the level 1 or level 2 arterial segment of the cerebral artery, and an outside diameter (OD) of 6F-10F, a proximal region having a stiffness greater than the stiffness of the soft distal tip region, the proximal region having a length sufficient to extend to outside the patient through the DEP.

12 Claims, 16 Drawing Sheets

(51) Int. Cl.

| | |
|---|---|
| *A61M 1/00* | (2006.01) |
| *A61M 25/00* | (2006.01) |
| *A61M 25/01* | (2006.01) |
| *A61F 7/00* | (2006.01) |

(52) U.S. Cl.
CPC ..................... *A61M 25/0108* (2013.01); *A61B 2017/22038* (2013.01); *A61B 2017/22079* (2013.01); *A61B 2017/22082* (2013.01); *A61F 2007/0056* (2013.01); *A61F 2007/126* (2013.01); *A61M 2210/0693* (2013.01)

(58) Field of Classification Search
CPC ................. A61B 2217/005; A61F 7/12; A61F 2007/0056; A61F 2007/126; A61M 1/75; A61M 25/008; A61M 25/0108; A61M 2210/0693

See application file for complete search history.

(56) References Cited

U.S. PATENT DOCUMENTS

| | | | | |
|---|---|---|---|---|
| 5,514,088 | A * | 5/1996 | Zakko ..................... | A61M 1/85 604/28 |
| 10,213,582 | B2 | 2/2019 | Garrison et al. | |

| | | | | |
|---|---|---|---|---|
| 10,456,555 | B2 | 10/2019 | Garrison et al. | |
| 10,646,239 | B2 | 5/2020 | Garrison et al. | |
| 11,871,944 | B2 | 1/2024 | Garrison et al. | |
| 11,925,770 | B2 | 3/2024 | Chou et al. | |
| 2004/0172222 | A1 * | 9/2004 | Simpson ................ | G08B 21/02 702/189 |
| 2005/0255442 | A1 * | 11/2005 | Brassil ................... | A61B 5/413 435/1.2 |
| 2012/0004596 | A1 * | 1/2012 | Thomas ......... | A61B 17/320758 606/159 |
| 2016/0296690 | A1 | 10/2016 | Kume et al. | |
| 2017/0239447 | A1 * | 8/2017 | Yang ..................... | A61M 25/10 |
| 2018/0064453 | A1 | 3/2018 | Garrison et al. | |
| 2018/0085167 | A1 | 3/2018 | Goyal | |
| 2018/0193042 | A1 | 7/2018 | Wilson et al. | |
| 2018/0207399 | A1 | 7/2018 | Chou et al. | |
| 2018/0250498 | A1 | 9/2018 | Stern et al. | |
| 2018/0256176 | A1 | 9/2018 | Cattaneo | |

OTHER PUBLICATIONS

European Patent Office, Extended European Search Report dated Jul. 13, 2022 in European Patent Application No. 20843137.9, 8 pages.

* cited by examiner

A

Prior Art

B

Prior Art

Y

50

ACt

AC

P1

CATHETER SYSTEMS ENABLING IMPROVED ASPIRATION FROM CEREBRAL ARTERIES

RELATED APPLICATIONS

This application is the U.S. National Phase of and claims priority to International Patent Application No. PCT/CA2020/051026, International Filing Date Jul. 24, 2020, entitled Catheter Systems Enabling Improved Aspiration from Cerebral Arteries; which claims benefit of and priority to U.S. Provisional Application Ser. No. 62/878,652 filed Jul. 25, 2019 entitled Catheter Systems Enabling Improved Aspiration from Cerebral Arteries; and U.S. Provisional Application Ser. No. 63/029,401 filed May 23, 2020 entitled Catheter Systems Enabling Improved Aspiration from Cerebral Arteries; all of which are incorporated herein by reference in their entireties.

FIELD OF THE INVENTION

The invention describes catheter systems and methods for accessing the brain during endovascular/neurointervention procedures in the treatment of ischemic stroke. More specifically, catheter systems are described that enable quicker and improved access to cerebral vessels as well as improved processes of accessing and aspirating blood clots from the cerebral vessels of a patient with acute ischemic stroke due to medium or large vessel occlusion.

BACKGROUND OF THE INVENTION

The human body is an extensive network of blood vessels including the venous and arterial systems for circulating blood throughout the body. The occurrence and/or development of restrictions to flow within the circulatory system can result in serious medical conditions, the most significant being myocardial infarction and ischemic stroke. The treatment of both conditions (and others involving the circulatory system) continues to evolve with many new techniques and equipment being utilized to effect various treatments.

As is known, ischemic strokes caused by blood clot blockages in the brain may be treated by advancing catheter systems to the affected site whence various procedures can be initiated to treat the problem. Known procedures include the deployment of various designs of catheters singularly and/or in conjunction with other catheters, stents and clot retrieval devices to gain access to and remove the clot.

By way of background, when a patient experiences a significant ischemic stroke event, those portions of the brain distal to the occlusion that experience a dramatic reduction in blood supply will affect the functioning of large regions of neurons. This reduction in blood supply may cause the patient to become symptomatic, cause the death of regions of the brain and/or put regions of the brain at the risk of dying if not treated quickly. Depending on the location and size of the occlusion will result in a wide range of symptoms in the patient and depending on the severity will ultimately determine how a physician may choose to intervene or not.

Time delays in effecting treatment will typically result in the death of a greater number of neurons. Table 1 shows that in the specific case of acute ischemic stroke, the pace or rate of neural circuitry loss in a typical large vessel supratentorial acute ischemic stroke can be very rapid.

TABLE 1

| | Estimated Pace of Neural Circuitry Loss in Typical Large Vessel, Supratentorial Acute Ischemic Stroke Estimated Pace of Neural Circuitry Loss in Typical Large Vessel, Supratentorial Acute Ischemic Stroke | | | |
| --- | --- | --- | --- | --- |
| | Neurons Lost | Synapses Lost | Myelinated Fibers Lost | Accelerated Aging |
| Per Stroke | 1.2 billion | 8.3 trillion | 7140 km/4470 miles | 36 yrs |
| Per Hour | 120 billion | 830 billion | 714 km/447 miles | 3.6 yrs |
| Per Minute | 1.9 million | 14 billion | 12 km/7.5 miles | 3.1 weeks |
| Per Second | 32,000 | 230 million | 200 meters/218 yards | 8.7 hours |

The numbers presented above represent an average with it also being known that there is a high degree of variability in the above numbers generally depending on the available blood supply to the ischemic region through collateral channels. Several factors including time delays in making a decision, time delays in commencing an endovascular procedure and delays during the procedure, any of which may only be in the order of only a few minutes, can have a significant impact on neural circuitry loss and ultimately patient outcome.

The paper "Analysis of Workflow and Time to Treatment and the Effects on Outcome in Endovascular Treatment of Acute Ischemic Stroke: Results from the SWIFT PRIME Randomized Controlled Trial" (Radiology. 2016 June; 279 (3):888-97. doi: 10.1148/radiol.2016160204. Epub 2016 Apr. 19), and incorporated herein by reference, quantitatively shows that there is a definitive improvement in patient outcome through fast reperfusion. In particular, this study concluded that "aggressive time goals may have contributed to efficient workflow environments". Further, the study quantifies inter alia that functional independence of a patient was significantly higher when treated quickly (i.e. within 2.5 hours of stroke onset).

Importantly, it is now known that efficient workflows during a recanalization procedure (of which the effectiveness and efficiency of a procedure is important) provides better outcomes.

Initially, in diagnosing ischemic stroke to assess possible treatments, it is important for the physician to know where the vessel occlusion is, how big the occlusion is, where any dead brain tissue ("core") is and, how big and where is the brain tissue that may have been affected by the ischemic event but that may potentially be saved ("penumbra").

The penumbra is tissue around the ischemic event that can potentially stay alive for several hours after the event by the perfusion of this tissue by collateral arteries. The collateral arteries may provide sufficient oxygen, nutrients and/or flushing to the penumbra tissue to prevent this tissue from dying for a period of time.

When responding to acute ischemic stroke, endovascular treatment of acute ischemic stroke due to large vessel occlusion in the anterior circulation is now the standard of care for patients under certain criteria. That is, patients exhibiting particular symptoms (i.e stroke symptoms of a particular severity) will benefit from early and rapid endovascular intervention to open occluded blood vessels. Generally, during various endovascular treatments, an interventionist will advance a series of catheters from the patient's groin through the femoral artery, descending aortic artery, to the aortic arch and into the cervical and cerebral arterial system towards the clot. After access to the clot is achieved by placement of the catheters, clot-retrieval and/or clot-suction devices are deployed through the catheter where the clot is either withdrawn and/or aspirated from the clot site. Access can also be gained from other areas including increasingly the radial artery and minimally through the carotid arteries.

There are many anatomical and situational considerations that can affect the severity and ultimately treatment of ischemic stroke. Importantly, as described above, while a blood clot may severely affect blood flow to the ischemic area, some blood flow may get to the ischemic area if collateral arteries are functioning to at least partially perfuse the affected area.

The most common large vessel occlusion that is treated by endovascular techniques is the M1 segment of the middle cerebral artery (MCA). When a patient has an M1 occlusion, the territory supplied by the M1 receives a dramatic reduction in blood supply. As a consequence, distal neurons don't function well and the patient becomes symptomatic.

Recanalization procedures utilize a wide range of equipment and techniques to access a clot and effect its removal. Generally, the endovascular surgeon will have several tools at their disposal including a wide range of guide catheters, balloon guide catheters, guide wires, diagnostic catheters, microcatheters, microwires, stents and other tools that individually have properties, features and functions that are effective for different procedures and patient presentations. Most, if not all of the above tools are disposable and they are also expensive. Hence, to the extent that similar or better results can be achieved utilizing faster procedures (i.e. in fewer steps), a smaller number of tools and/or at a lower cost, there is a motivation to continue to design new tools that can achieve these objectives. Moreover, minimizing the number of catheters that are utilized can help reduce the potential for errors and/or undesired consequences that can result from complex procedures.

As noted, endovascular procedures into the brain are typically performed by gaining access to the arterial vascular system through the patient's groin area by puncturing the common femoral artery and inserting an arterial sheath.

Then, under fluoroscopic (Xray) guidance, a catheter system (usually a co-axial system including a guide catheter (GC) or balloon guide catheter (BGC), diagnostic catheter (DC) and guide wire (GVV)) is advanced through the descending aorta to reach the aortic arch.

The diagnostic catheter has a shaped tip and is used to hook the vessel of interest and with the help of a guidewire, the diagnostic catheter is advanced to the desired artery. Subsequently the guide catheter/balloon guide catheter is advanced over the diagnostic catheter such that the tip of GC/BGC is in the desired cervical artery.

At this stage, the diagnostic catheter and wire are removed such that the GC/BGC provides a direct conduit from outside the body to the cervical artery of interest. It should be noted that the GC/BGC takes up space and has an outside or outer diameter (OD) and an internal or inner diameter (ID) that limits the size of all further equipment that is advanced through the GC/BGC. The maximum OD of the GC/BGC is governed inter alia by the ID of the arterial sheath.

Subsequently, catheters that are designed for intracranial access are advanced through the guide catheter. This will typically consist of one of two approaches:

a. a microcatheter and a microwire; or, b. a tri-axial system comprising of a distal access catheter (DAC), a microcatheter and a microwire.

For approach a: once the clot has been crossed by the microcatheter and microwire, the microwire is removed and a stent-retriever is slowly deployed across the clot. While aspirating through the guide catheter (with the balloon inflated if using a BGC) the stent-retriever is withdrawn to capture the clot and establish reperfusion.

For approach b: the DAC is placed proximal to the clot. In one approach b1, the microcatheter is used to cross the clot and after removal of the microwire, a stent retriever is deployed. Then the stent-retriever and DAC are typically withdrawn together, while aspirating from the DAC. In a second approach b2, a stent retriever is not used and directly an attempt is made to capture the clot by aspirating through the DAC.

There are a range of problems and/or limitations with advancing catheter and/or stent-retriever systems to a clot and conducting a procedure including the highly complicated and variable physical dimensions of the patient's anatomy.

For example, one particular consideration is that stroke typically affects the elderly and with increasing age, there is usually an increase in tortuosity of the aortic arch often making it difficult to access the cervical arteries. In particular, a highly tortuous combination of aortic arch and carotid artery can be difficult to advance catheter systems through as high bend angles and friction may cause catheters to prolapse into the ascending aorta and thus fail to advance through the desired vessel. In other words, when pushing a catheter system through tight bends, the system will seek the path of least resistance and can end up being pushed in a wrong direction. In addition, tortuosity may prevent further advancement of the catheter. The combination of a sharp turn and an origin of another artery, as is commonly seen in the ophthalmic segment of the internal carotid artery can be a common place where such a catheter can get stuck.

Another consideration is the size of the available catheter systems and the issues around the need to provide GC/BGC support to smaller catheters to advance them. With smaller catheters being supported by a larger catheter, the OD/ID of the smaller, internal catheters is limited by the ID of the larger support catheter.

Catheter Performance

As mentioned above, two categories of catheters used in cerebral procedures namely diagnostic and guide catheters. Diagnostic catheters are generally those used to gain access to an area of interest whereas guiding catheters are used to support and guide additional equipment including diagnostic catheters, guidewires, balloons, microcatheters, stents, microwires etc. as may be required for a particular surgical technique.

Typical diagnostic catheters will range from 4F to 6F (French) and have lengths of 65-125 cm. They may have braided wall structures and they will generally have a soft tip with a range of shapes formed into the tip typically to enhance hooking of a particular vessel. Different stiffnesses can be designed into the DC and be relatively soft or stiff.

Guide catheters are generally larger (e.g. 6-9F) and are typically 80-100 cm in length. They generally have reinforced construction with a significantly stiffer shaft to provide back-up (i.e. retro) support for the advancement of any additional equipment as listed above. However, guide catheters can generally only be advanced as far as the carotid artery in the neck as the combination of their stiffness, the narrowing of vessels and the curvature of vessels prevents further advancement.

From an anatomical perspective, catheters necessarily pass through different zones of the vasculature, namely the abdominal and thoracic vasculature between the femoral artery and aortic arch (approximately 50-75 cm) in the example of catheters entering the body via a groin puncture, the cervical vasculature (approximately 15-20 cm) and the cephalic/cerebral vasculature (approximately 10-15 cm). The vessels progressively narrow from 2.5 cm in the aorta down to 3 mm and smaller in the cerebral vessels.

Various properties and geometries may be engineered into both diagnostic and guide catheters including:

Trackability—the ability of the catheter to slide over a guide wire particularly through tortuous (tightly curved) vessels.

Pushability—the ability to advance the tip or head of the catheter based on the input from the operator from the hub (i.e. from outside the body).

Torquability—the ability to steer the tip of the catheter based on twisting at the hub by the operator.

Tip or head shape—the shape of the tip or head of the catheter will assist the operator in navigating the distal tip of the catheter through particular anatomical features. For example, a diagnostic catheter may have a flush, straight, simple curve, complex curve, reverse curve or double curve shapes inter alia. Such shapes may be categorized as simple or complex.

Stiffness—the ability of a catheter to bend around a curve and support a catheter moving within it.

Catheter Construction

Each catheter may be constructed from a plurality of materials, having various structures and/or layers within the catheter wall structure to give the catheter particular properties or functional characteristics. These may include:

Surface Coatings—Surface coatings desirably reduce thrombogenicity, have low friction coefficients and/or anti-microbial characteristics.

Reinforcement—Internal wire braiding is used to impart torque control/stiffness characteristics to the catheter.

Polymer Layers—Different polymers may be used to give different structural characteristics to the body of the catheter. For example, Polyurethanes can be soft and pliable and hence follow guide wires more effectively. However, they have a higher coefficient of friction.

Nylon may be used for stiffness and be able to tolerate higher flow rates of fluids through them.

The choice of a particular catheter or system of catheters is typically determined by the skill, experience and preferences of a particular interventionist.

Some typical properties of different catheters are summarized in Table 2.

TABLE 2

| | Summary of Catheter Properties | | | |
|---|---|---|---|---|
| Catheter | Body Properties | Diameter | Typical Length | Typical Tip Features |
| Guide Catheter/ Balloon Guide Catheter | Usually quite stiff Atraumatic tip Supports and guides other catheters Double lumen if Balloon Guide Catheter (BGC) | 6-8 F | Extracorporeal + Groin to Carotid 80-100 cm | May have balloon |
| Diagnostic Catheter | Variable Tip Stiffness Variable Tip Shapes Torquable | 4-6 F | Extracorporeal + Groin to Carotid 100-125 cm | Soft Tip Multiple Shapes |
| Microcatheter | Soft Tip Pushable Trackable | 1-5-2.5 F | Advanced through and is supported by the guide catheter Travel to intracranial vessels (over a microwire) and to beyond the clot. 150 cm | Rounded Soft Tip |
| Guide Wire | Pushable Torquable | 1 F | Travels inside diagnostic catheter or guide catheter (used to advance these catheters to the cervical carotid artery) 150-300 cm | Rounded |
| Reperfusion/ Aspiration Catheter | Multizone (may be up to 12-15 zones) Increasing level of softness distally to allow the catheter to negotiate significant tortuosity and remain atraumatic Distal transition zones may extend for 30-40 cm) Enables two-way Fluid Flow Pushable | 4-6 F (diameter may be greater proximally to allow for better suction. | Travel inside the guide catheter. Usually over a microcatheter Extracorporeal + Groin to Occlusion 105-125 cm | Rounded Soft Tip Challenging design to prevent ovalization during passing through significant curvature and while applying suction. |

TABLE 2-continued

| | | Summary of Catheter Properties | | |
|---|---|---|---|---|
| Catheter | Body Properties | Diameter | Typical Length | Typical Tip Features |
| Stent-Retriever (Clot Retrieval System) | Integrated Clot Retrieval System Pushable | very small in its collapsed state (travel through microcatheter). In expanded state: 3-6 mm | Extracorporeal + Groin to Occlusion 180 cm Travel through microcatheter. | Integrated Clot Retrieval System |
| Microwire | Pushable Torquable 10-16/1000 of an inch soft atraumatic tip | 180-200 cm travels through microcatheter | extracorporeal to intracranially (beyond the clot) | round soft tip. |

Typical Endovascular Procedures for Treatment of Ischemic Stroke

As noted above, when an endovascular surgeon begins a procedure, access to the vasculature is typically obtained through the groin; however, as discussed below, other areas of access including the radial artery are increasingly being used.

After groin puncture, variations of the following steps are performed to advance different catheters through the vasculature to a site of interest. Typically, in the case of a procedure using a balloon guide catheter and stent (i.e a clot retrieval device), these steps include:

Step A—Aortic Arch Access
  a) Following groin puncture, a sheath is deployed. The sheath acts as an access port to the body and will be inserted typically 15 cm into the femoral artery. The sheath has an ID of approximately 8F. Longer sheaths (generally 45 cm long can be used if there is significant tortuousity in the femoral and iliac arteries.
  b) An assembly of a guide catheter (GC)/balloon guide catheter (BGC), a diagnostic catheter (DC) and guide wire (GW) is advanced to the aortic arch. The GC/BGC will typically have an OD of 8F (matching the sheath). The DC (OD 4-6 F) is retained inside the BGC and the GW (OD 0.035") is retained within the DC.
Step B—Carotid and Cerebral Artery Access
  a) The DC is manipulated to gain access to the desired carotid artery.
  b) After gaining access to the carotid artery, the GW is advanced, typically up to 20-30 cm towards the occlusion site (but within the cervical carotid arteries).
  c) After the GW has been advanced (or concurrently and/or sequentially), the DC is advanced over the GW to gain access to the occlusion site. This may occur in a concurrent and/or sequential process depending on the particulars of a particular patient. However, this step can have significant problems. The design of the DC is to enable hooking the relevant vessel. Typically, the tip (distal 5 cm) is pre-shaped and overall the diagnostic catheter is stiff and torquable. These properties make it possible to hook the vessel but can thereafter work against the interventionist as the DC is advanced over the wire. That is, the relative stiffness of the DC tip within the cervical artery may prevent it from sliding over the GW and cause the whole system to prolapse into the ascending aorta.
  d) An alternative approach is to not advance the DC but instead advance the BGC while leaving the DC in position at the origin of the vessel. This solution does work sometimes but often also has the same problem due to the stiffness of the guide catheter.
Step C—Guide Catheter (GC)/Balloon Guide Catheter (BGC) Placement
  a) The GC/BGC is advanced over the DC and GW to gain access to the cervical arteries, typically a straight segment of the cervical internal carotid artery.
  b) The DC and GW are then fully removed.
Step D—Microcatheter/Microwire Placement
  a) A microcatheter (MC) and microwire (MW) are advanced together through the BGC all the way to the clot such that the distal tip of the MC and MW are positioned just past the distal edge of the clot.
  b) Once the MC is positioned, the MW is removed.
Step E—Stent Deployment
  a) A stent (i.e. clot retrieval device) is advanced through the MC until the distal tip of the stent is adjacent the distal end of the MC.
  b) The stent is unsheathed by pulling back on the MC while holding the stent in position. As the stent is unsheathed it will expand into clot to engage with the clot.
Step F—Clot Removal
  a) The BGC is inflated to stop antegrade flow and retrograde flow (suction) through the BGC is initiated.
  b) Simultaneously, the stent which is now engaged with the clot, together with the MC is pulled proximally through the BGC to outside of the body.
  c) A check angiogram is performed through the BGC to see if the clot retrieval has been successful. If not the steps E and F may be repeated.
  d) Once successful reperfusion has been achieved the BGC, stent and clot are removed from the body.
Variations In variations of the procedure, a distal access catheter (DAC) (4-6.0 F) may be added to the procedure. This can be done one of two ways:

A—Aspiration Technique.
  i. In this technique, after access to the cervical internal carotid artery has been achieved using a guide catheter and DC, the guide catheter (GC) which may nor may not be a BGC is placed in the cervical internal carotid artery.
  ii. The DC is removed
  iii. A tri-axial system consisting of a DAC, a MC and MW are advanced towards the intracranial circulation with the aim of having the tip of the DAC (Aspiration catheter) reach the face of the clot. An integrated support catheter (ISC) as described in U.S. Pat. No. 10,456,552 and incorporated herein by reference, may be used to improve/assist movement through these arterial systems. For achieving this it is possible that the MC and MW may have to be placed beyond the clot. Typically, in this case, the DAC will have a maximum size of 6F. Larger size catheters are not possible as they require larger guide catheters to support them in the neck and do not have sufficient distal flexibility to enable navigation/negotiation through tighter curves.

iv. The MW and MC (and/or ISC) are removed.

v. With the DAC at the face of the clot, suction through the DAC is applied until there is successful retrieval of clot or the endovascular surgeon decides to try an alternative approach. Local suction has an advantage that more of the suction pressure is likely to be transmitted to the clot. However, as described below, there are several possible outcomes when aspiration is applied. Other disadvantages of DACs are discussed below.

B—Solumbra Technique i. The initial part of this technique is the same as the Aspiration technique (i.e steps A(i)-a(iii)).

ii. However, once the MC is beyond the clot and the DAC is at the face of the clot, the MW is removed and a stent is deployed across the clot.

iii. Then, while applying suction to the DAC, the MC and stent are withdrawn. Thus, the suction pressure is right next to the clot rather than from the neck as with a BGC. Also, the stent enters the DAC while still in the intracranial vessels thus reducing the likelihood of losing the clot once it has been captured.

In cases where the aspiration techniques without using a stent are not successful in removing the clot, with a BGC in place, a GW, MC and stent may be subsequently deployed.

In both techniques, the application of suction pressure can result in a variety of outcomes. Generally speaking, typical DACs (aspiration catheters) will be smaller than most clots where the DACs will have a maximum ID in the range of 0.053-0.068" (with corresponding ODs of 6F) whereas the size/OD of the clot will be the same size as the ID of the vessel that it lodges in (the clot is typically an embolus from a more proximal source such as the heart or the carotid artery; it will keep traveling distally till the size of the embolus matches the size of the vessel). Thus, there will be a difference between the size of the distal tip opening of the DAC and the clot and/or the vessel. In addition, most intracranial vessels are quite tortuous and as the DAC is being advanced it will have a tendency to stay on the outer aspect of the curve. As a result, the distal tip of the DAC may not be perpendicular to the vessel wall and/or partially separated from the vessel wall such that the clot may partially engage with an outer edge of the DAC.

In addition, in cases where the clot is "significantly" larger than the DAC, aspiration through the distal tip of the DAC will generally not achieve ingestion of the clot but rather the proximal most part of the clot gets 'corked' into the distal tip of the DAC and cannot be pulled into the DAC during aspiration as most clots are not that compressible.

Importantly, as the properties of the clot are highly variable in terms of consistency/rigidity/internal cohesion etc., the ultimate application of suction and/or proximal pressure may result in:

a) The entirety of the clot being ingested into the DAC (desired).

b) The clot partially breaking into one or more smaller pieces and proximal piece(s) being fully ingested into the DAC which may result in piece(s) moving distally (not desired).

c) The clot not being ingested into the DAC and plugging the distal tip thus requiring the DAC to be withdrawn with the clot only partially ingested (favorable end result but may not be rapid).

d) As in c) fibrin rich zones of the clot may get stuck in the DAC requiring withdrawal of the DAC to remove a section of the clot. In some cases, the clot may also have less fibrin rich zones which can then break away from the stuck part with smaller piece(s) then moving further distally (not desirable).

e) The clot not fully engaging with the DAC and/or not being ingested resulting in the clot remaining where it is (which may then cause the surgeon to consider deploying a stent; less desirable).

Overall, of all these possibilities, complete ingestion of the clot is the most desirable as this a) prevents fragmentation, b) prevents distal emboli and c) as the more proximal part of the clot gets sucked into the catheter, the suction pressure gets transmitted to the next portion of the clot. However, as noted above DACs have generally had an upper limit in size which can thus result in a higher mismatch of sizes between the vessel/clot and the DAC.

Furthermore, once a clot is believed to have been captured, it is generally necessary to fully withdraw the DAC from the body to enable a check angiogram to be conducted. The check angiogram is conducted to determine if the clot has been fully removed and to determine if any smaller pieces have been left behind.

As noted, BGCs are used to enable the surgeon to stop antegrade blood flow and are necessary to minimize the risk in cases where the DAC is being withdrawn with a partially-ingested clot for the clot to shear and embolize distally. That is, as the diameter of the clot (and stent if being used) can be larger than the inner lumen of the BGC, as the DAC is being withdrawn (with or without the stent), there is a significant chance of part of the clot being sheared off and embolizing distally. Hence cessation of antegrade flow by inflating the balloon reduces the risk of this happening. However, the use of a BGC reduces the size of the DAC as the DAC must be within the BGC.

Hence, to the extent that it is possible to advance a single large OD catheter (eg. 7F or greater) from the groin to a clot (eg. at a M2 level or higher) such that a larger opening distal opening is available to fully engage with a blood clot without simply holding only its proximal end at the tip due to suction pressure but rather fully ingesting it, the risk of causing a distal emboli, the time to complete an aspiration procedure and the cost of conducting such a procedure can be substantially reduced. However, challenges include the ability to advance large OD catheters into the cerebral arteries due to the difficulty in manipulating such devices through tight curves and the common practice of using them within a GC/BGC.

Further still, in the era of coronavirus, hospital treatment procedures have been altered to minimize the risk to all health workers and the patient with the result being stricter separation between personnel when preparing for and conducting procedures. Such separation procedures decrease the efficiency of the medical procedures as it takes more time to move equipment between designated areas. Accordingly, there now exists increased motivation to design equipment, kits and processes that overcome inefficiencies that have emerged as a result of the coronavirus.

SUMMARY OF THE INVENTION

In accordance with the invention, there are provided systems and methods for improving the efficiency and effectiveness of surgical procedures.

In a first aspect, the invention provides a distal entry point (DEP) to brain aspiration (D2BA) catheter for use in an endovascular procedure for gaining access to cervical and cerebral arteries in a brain of a patient and aspirating one or more intracranial clots from the cerebral arteries, the D2BA catheter for placement within the human vasculature of the patient between the DEP and the cerebral arteries in the brain, comprising: a soft distal tip region having a distal length sufficient to extend from a level 1 or level 2 arterial segment of a cerebral artery or equivalent to an upper neck arterial vessel, the soft distal tip region having a stiffness enabling movement through the level 1 or level 2 arterial segment of the cerebral artery, and an outside diameter (OD) of 6F-10F; and a proximal region having a stiffness greater than the stiffness of the soft distal tip region, the proximal region having a length sufficient to extend to outside the patient through the DEP; wherein the D2BA catheter enables aspiration through the D2BA catheter to remove the one or more clots.

In various embodiments:

The soft distal tip and proximal regions have sufficient flexibility and axial and radial compressive rigidity to enable the soft distal tip region to be advanced over a guide wire (GW) and a diagnostic catheter (DC) to position a distal tip of the soft distal tip region at an upper cervical/close-to-base-of-skull location without an external support catheter.

The soft distal tip and proximal regions have sufficient flexibility and axial and radial compressive rigidity to enable, when the soft distal tip region is at an upper cervical/close-to-base-of-skull location having been advanced over a guide wire (GW) and diagnostic catheter (DC), withdrawal of the guide wire and diagnostic catheter does not prolapse the D2BA catheter from the cervical arteries.

The soft distal tip and proximal regions have sufficient flexibility and axial and radial compressive rigidity where when the GW and DC have been withdrawn, a microwire (MW) and integrated support catheter (ISC) can be advanced through the D2BA catheter to the distal tip and the D2BA catheter can be further advanced over the MW and ISC to a position where the distal tip substantially engages with a cerebral artery wall adjacent a clot.

The D2BA catheter has a wall thickness of 0.013" or less.

The outside diameter (OD) of the D2BA catheter is 7 F and the distal length extends from the upper neck arterial vessel to level 2 segments of the middle cerebral artery or from the distal cervical vertebral artery to the basilar artery or equivalent.

The distal length is 17-25 cm.

The outside diameter (OD) of the D2BA catheter is 8 F and the distal length extends from the upper neck arterial vessel to distal level 1 segments of the middle cerebral artery.

The distal length is 15-23 cm.

The outside diameter (OD) of the D2BA catheter is 9 F and the distal length extends from the upper neck arterial vessel to proximal level 1 segments of the middle cerebral artery or equivalent.

The distal length is 13-21 cm.

The outside diameter (OD) of the D2BA catheter is 10 F and the distal length extends from the upper neck arterial vessel to distal segments of the internal carotid artery or equivalent.

The distal length is 12-16 cm.

The soft distal tip region comprises at least one polymeric section having a composition providing axial stiffness and flexibility to a specific linear position of the D2BA catheter.

The proximal region comprises at least one polymeric section having a composition providing axial stiffness and flexibility to a specific linear position of the D2BA catheter.

The D2BA catheter has a torsional stiffness that enables torque applied to the proximal zone to be transmitted to the distal tip of the distal zone enabling rotational movement of the distal tip within a vessel and where the distal tip defines an oblique angle in a range of 10-30 degrees with respect to a perpendicular cross section of the D2BA catheter.

In another aspect the invention provides an endovascular catheter system comprising: a D2BA catheter; and a second aspiration catheter having an outside diameter maximized for operative movement within the D2BA catheter and having a length sufficient to extend to a position substantially equivalent to the distal tip of the D2BA catheter, the second aspiration catheter configured to enable positioning adjacent the distal tip of the D2BA catheter and to apply suction pressure to a proximal edge of a clot through the second aspiration catheter while within the D2BA catheter. In one embodiment, the second aspiration catheter has a proximal end and proximal end lock, the proximal end lock engageable with a proximal region of the D2BA catheter to prevent the second aspiration catheter from extending beyond the distal tip of the D2BA catheter.

In another aspect the invention provides an endovascular catheter system comprising: a D2BA catheter and a cooling catheter having an outside diameter maximized for operative movement within the D2BA catheter and having a length sufficient to extend to a position substantially equivalent to the distal tip of the D2BA catheter, the cooling catheter configured to convey a cooling fluid through the cooling catheter to the distal tip of the D2BA catheter and where the combination of the D2BA catheter and cooling catheter provides sufficient insulation to enable effective flow of cooling fluid through the insulation catheter to enable effective cooling of brain tissue after clot removal.

In various embodiments:

The outside diameter (OD) of the D2BA catheter is 8F and the outside diameter (OD) of the cooling catheter is substantially 6F and the cooling catheter has a wall thickness of 0.020-0.03" and preferably 0.026".

The wall thickness of the cooling catheter is substantially consistent along the length of the cooling catheter and includes insulation to the distal tip of the cooling catheter.

In another aspect the invention provides an endovascular catheter system comprising: a D2BA catheter and a secondary D2BA catheter having an outside diameter maximized for operative movement within the D2BA catheter and having a length sufficient to extend to a position beyond the distal tip of the D2BA catheter, the secondary D2BA catheter configured to enable advancement of the secondary D2BA catheter to a position beyond the distal tip of the D2BA catheter and to apply suction pressure to a proximal edge of a secondary clot distal to the clot through the secondary D2BA catheter.

In another aspect the invention provides an endovascular catheter system comprising: a D2BA catheter; a diagnostic catheter (DC) and guide wire (GW) for internally supporting advancement of the D2BA catheter to the cervical arteries; an integrated support catheter (ISC) having an outside diameter maximized for operative movement within the D2BA catheter, a length sufficient to extend to a position beyond the distal tip of the D2BA catheter and a distal taper for supporting the distal tip of the D2BA catheter while advancing the D2BA catheter into the cerebral arteries; a microwire (MW) configured for operative movement within the ISC and having a length sufficient to extend to a position beyond a distal tip of the ISC for advancing the ISC and D2BA catheter into the cerebral arteries; a secondary D2BA catheter having an outside diameter maximized for operative movement within the D2BA catheter and having a length sufficient to extend to a position beyond the distal tip of the D2BA catheter, the secondary D2BA catheter configured to enable advancement of the secondary D2BA catheter to a position beyond the distal tip of the D2BA catheter and to apply suction pressure to a proximal edge of a secondary clot distal to the clot through the secondary D2BA catheter; a secondary integrated support catheter (ISC) having an outside diameter maximized for operative movement within the secondary D2BA catheter and having a length sufficient to extend to a position beyond to the distal tip of the secondary D2BA catheter; and a secondary microwire (MW) configured for operative movement within the secondary ISC and having a length sufficient to extend to a position beyond a distal tip of the secondary ISC.

In another aspect the invention provides an endovascular catheter system comprising: a D2BA catheter; and a stent configured for operative movement within the D2BA catheter, the stent operatively connected to a push wire having a length sufficient to extend to a position beyond the distal tip of the D2BA catheter to enable deployment of the stent from the distal tip of the D2BA catheter.

In another aspect the invention provides a kit for use in an endovascular procedure for gaining access to cervical and cerebral arteries and aspirating intracranial clots from the cerebral arteries, comprising: an endovascular catheter for placement within the human vasculature between a distal entry point (DEP) and cerebral arteries comprising a D2BA catheter; at least one diagnostic catheter (DC), each DC having an outside diameter to fit and slide within the D2BA catheter and each DC having a pre-shaped tip for accessing varying anatomies of an aortic arch and having a length longer than the D2BA catheter; and a guide wire (GW) having a diameter to fit and slide within the DC and having a length longer than the DC.

In various embodiments:

The kit further includes an internal support catheter (ISC), the ISC having an outside diameter to fit and slide within the D2BA catheter and a tapered distal zone for supporting and transitioning the distal tip of the D2BA catheter in tightly curved arteries during advancement of the D2BA catheter into the cerebral arteries.

The kit has two or more DCs.

The kit includes an aspiration catheter having an outside diameter maximized for operative movement within the D2BA catheter and having a length sufficient to extend to a position substantially equivalent to the distal tip of the D2BA catheter.

The kit includes a cooling catheter having an outside diameter maximized for operative movement within the D2BA catheter and having a length sufficient to extend to a position substantially equivalent to the distal tip of the D2BA catheter.

The kit includes a second D2BA catheter sized to fit within the D2BA catheter and a corresponding second ISC and second MW sized to fit in the second D2BA catheter each having lengths greater than the D2BA catheter.

In another aspect the invention provides a cooling catheter for conveying an effective volume of a cooling liquid through a D2BA catheter, the cooling catheter comprising a catheter having an outside diameter maximized for operative movement within the D2BA catheter and having a length sufficient to extend to a position substantially equivalent to a distal tip of the D2BA catheter, the cooling catheter configured to convey a cooling fluid through the cooling catheter to the distal tip of the D2BA catheter and where the combination of the D2BA catheter and cooling catheter provides sufficient insulation to enable effective flow of cooling fluid through the insulation catheter to enable effective cooling of brain tissue after clot removal. In one embodiment, the wall thickness of the cooling catheter is substantially consistent along the length of the cooling catheter and includes insulation to the distal tip of the cooling catheter.

In another aspect the invention provides an endovascular method for gaining access to cervical and cerebral arteries, the endovascular method for placing a catheter system within the human vasculature between a distal entry point (DEP) and cerebral arteries and aspirating a cerebral clot in one of the cerebral arteries, the method comprising the steps of:

a) introducing a catheter system including a D2BA catheter, guide wire (GW) and diagnostic catheter (DC) through a DEP;

b) advancing the catheter system to an aortic arch;

c) advancing the GW and DC to a desired cervical artery and manipulating the GW into a desired cervical artery;

d) advancing the D2BA catheter to a desired carotid artery over the DC and GW;

e) removing the DC and GW;

f) introducing an internal support catheter (ISC) having a tapered distal section for supporting a distal end of the D2BA catheter and adapted to facilitate movement of the distal end through tight curves in the cerebral vasculature and an ISC microwire (ISC MW);

g) advancing the ISC and ISC MW to the cerebral artery with the clot;

h) advancing the D2BA catheter to a proximal face of the clot and withdrawing the ISC and ISC MW; and, i) applying suction to the clot through the D2BA catheter.

In another embodiment, the method further comprises the steps of:

j) after applying suction to withdraw a clot in step i, conducting a check angiogram to determine if the entire clot has been withdrawn and if one or more distal emboli are present and if present;

k) advancing a second D2BA catheter sized for co-axial movement within the D2BA catheter together with a second ISC and second ISC MW to a proximal face of the distal emboli; and, l) applying suction to the second D2BA catheter to withdraw the distal emboli via aspiration or by withdrawing the second D2BA catheter.

In various embodiments:

The DEP is a radial artery and the D2BA catheter has a proximal length adapted for advancement from a radial artery puncture.

The DEP is a femoral artery and the D2BA catheter has a proximal length adapted for advancement from a femoral artery puncture.

Step i includes applying one or more first pressure pulses through the D2BA catheter to assist in engaging the distal tip of the D2BA catheter against the clot followed by at least one second aspiration pulse to aspirate the clot.

The method includes the step of comparing a pre-determined pressure pulse against a measured response pressure at a suction pump and adjusting subsequent pressure pulses based on the measured response pressure.

The step of adjusting subsequent pressure pulses considers pressure response data from a plurality of patients collected and analysed from similar procedures.

Suction is applied via a suction pump operatively connected to the internet and a central analysing computer system and wherein pressure response data from different pumps is received and analysed by the central computer system and wherein pump pressure algorithms are updated via the internet to the different pumps.

Pump pressure algorithms consider catheter materials, brand and/or size.

If aspiration has been unsuccessful, an aspiration catheter is introduced into the D2BA catheter and the aspiration catheter is advanced to the distal tip of the D2BA catheter and suction is applied through the D2BA catheter.

If aspiration has been successful, a cooling catheter is introduced into the D2BA catheter and the cooling catheter is advanced to the distal tip of the D2BA catheter and a cooling fluid is flushed through the cooling catheter to effect cooling of brain tissue.

The method includes flushing brain nourishing solution through the cooling catheter.

The cooling catheter is an ISO having proximal insulation and where after the ISO has been withdrawn and aspiration has been completed, the ISO is re-introduced and brain nourishing solution is flushed through the ISO.

In another aspect, the invention provides a method for enabling effective removal of a heterogeneous clot having a fibrin-rich region and a red blood cell rich region from a cerebral vessel comprising the steps of:

a) positioning a D2BA catheter adjacent a proximal edge of a clot in the cerebral vessel;

b) applying a first pressure pulse to effect aspiration of a first proximal region of the clot; and c) applying a second pressure pulse to effect aspiration of a second distal region of the clot.

In various embodiments:

The first proximal region is a fibrin-rich region and the second distal region is an RBC rich region.

The method includes monitoring a first returned pressure wave after delivery of the first pressure pulse and adjusts the second pressure pulse based on the first returned pressure wave.

In another aspect, the invention provides a cooling apparatus for controlling temperature of a cooling liquid delivered through a cooling catheter comprising: a fluid cooling module for delivering cooling liquid to a proximal end of a cooling catheter, the fluid cooling module having: a fluid pump and controller for pumping a calculated volume of cooling liquid through the cooling catheter, the calculated volume based on modelling of heat transfer through the cooling catheter, modelled data of a D2BA as selected for a patient, patient data and a desired cooling liquid temperature at a distal end of the cooling catheter.

In another aspect, the invention provides the use of a D2BA catheter for accessing a cerebral artery without guide catheter support and applying suction to one or more intracranial clots from the cerebral arteries, the D2BA catheter for placement within the human vasculature between a distal entry point (DEP) and cerebral arteries comprising: a soft distal tip region having a distal length sufficient to extend from a level 1 or level 2 arterial segment or equivalent to an upper neck/close-to-base-of-skull arterial vessel, the soft distal tip region having an outside diameter (OD) 6F-10F; a proximal region connected to the soft distal tip region at a junction, the proximal region having a length sufficient to extend to outside the patient through the DEP and having an OD substantially similar to the soft distal tip region ID; and wherein the D2BA catheter enables aspiration through the D2BA catheter to remove the one or more clots.

In one embodiment, the soft distal tip and proximal regions have sufficient flexibility and axial and radial compressive rigidity in balance with respect to each other enabling the soft distal tip region to be advanced over a guide wire (GW) and diagnostic catheter (DC) to position a distal tip of the soft distal tip region at a upper neck/close-to-base-of-skull location without an external support catheter.

In another embodiment, the soft distal tip and proximal regions have sufficient flexibility and axial and radial compressive rigidity in balance with respect to each other enabling, when the soft distal tip region is at an upper neck/close-to-base-of-skull location having been advanced over a guide wire (GW) and diagnostic catheter (DC), withdrawal of the guide wire and diagnostic catheter does not prolapse the D2BA catheter from the cervical arteries.

In another embodiment, the soft distal tip and proximal regions have sufficient flexibility and axial and radial compressive rigidity in balance with respect to each other where when the GW and DC have been withdrawn, a microwire (MW) and integrated support catheter (ISC) can be advanced through the D2BA catheter to the distal tip and the D2BA catheter can be further advanced over the MW and ISC to a position where the distal tip substantially engages with a cerebral artery wall adjacent a clot.

In another aspect, the invention provides an endovascular catheter for use in an endovascular procedure, the endovascular catheter having a structure for gaining access to cervical and cerebral arteries and aspirating one or more intracranial blood clots from the cerebral arteries, the endovascular catheter for placement within the human vasculature between a distal entry point (DEP) and cerebral arteries comprising: a soft distal tip region having a distal length sufficient to extend from a level 1 or level 2 arterial segment of the cerebral arteries or equivalent to an upper neck/close-to-base-of-skull arterial vessel, the soft distal tip region having an outside diameter (OD) 6F-10F wherein the soft distal tip region has a flexibility to ride over a diagnostic catheter (DC) and guide wire (GW) positioned within cervical arteries to gain access to the cervical arteries through the aortic arch without causing prolapse of the DC and GW and where upon removal of the DC and GW, the D2BA catheter can be further advanced to cerebral arteries; a proximal region transitioning to the soft distal tip region, the proximal region having a length sufficient to extend to outside the patient through the DEP; wherein the D2BA catheter can be advanced to cervical arteries without guide catheter support.

In another aspect, the invention provides a distal entry point to brain aspiration (D2BA) catheter having an outside diameter greater than 6F and a length sufficient to extend from an extracorporeal distal entry point (DEP) to a blood clot in a level 1 or level 2 segment of a cerebral artery, the D2BA catheter having sufficient axial flexibility/stiffness along its length to advance the D2BA catheter from the DEP over a guide wire (GW) and diagnostic catheter (DC) to distal tips of the GW and DC when the GW and DC are positioned at an upper cervical/close-to-base-of-skull level and wherein the D2BA catheter can be advanced through the aortic arch with support only by the GW and DC.

In another aspect, the invention provides a distal entry point to brain aspiration (D2BA) catheter comprising a catheter having: an outside diameter 6F-10F; a length sufficient to extend from an extracorporeal distal entry point (DEP) to a cerebral artery blood clot; a soft distal tip zone having an axial flexibility/stiffness along its length to advance the D2BA catheter from the DEP over a guide wire (GW) and diagnostic catheter (DC) to distal tips of the GW and DC when the GW and DC are positioned at an upper cervical/close-to-base-of-skull level, the soft distal tip zone having a distal tip outside diameter selected to substantially match the inside diameter of an artery where the blood clot is positioned and a length to extend from the blood clot to the upper cervical/close-to-base-of-skull level; a proximal zone having an axial flexibility/stiffness along its length to advance the D2BA catheter and wherein the soft distal tip zone can be advanced through the aortic arch with support only by the GW and DC.

In another aspect, the invention provides an aspiration catheter (AC) having an outside diameter greater than 6F and a length sufficient to extend from a distal entry point (DEP) to a level 1 arterial segment of the brain or higher wherein the AC has a distal region and proximal region having a combined axial flexibility and stiffness enabling: the AC to be advanced over a diagnostic catheter (DC) and guide wire (GVV) positioned between the DEP and the cervical arteries without prolapsing the DC and GW and without guide catheter (GC) support; the DC and GW to be withdrawn from the AC without prolapsing the AC; the AC to be advanced to a blood clot at the level 1 arterial segment or higher in conjunction with at least one microcatheter (MC) and microwire (MW); and, aspiration through the AC to effect suction on the blood clot.

In another aspect, the invention provides an aspriation catheter (AC) comprising a catheter having an outside diameter 6F-10F and a length sufficient to extend from a distal entry point (DEP) to a blood clot in a cerebral artery wherein the AC has a distal region having a distal tip having a distal tip outside diameter substantially corresponding to the inside diameter of the cerebral artery where the blood clot is located and a length extending from the blood clot to an upper cervical/close-to-base-of-skull level and where the distal region and proximal region have a combined axial flexibility and stiffness enabling: the AC to be advanced over a diagnostic catheter (DC) and guide wire (GW) positioned between the DEP and the cervical arteries without prolapsing the DC and GW and without guide catheter (GC) support; the DC and GW to be withdrawn from the AC without prolapsing the AC; the AC to be advanced to the blood clot in conjunction with at least one microcatheter (MC) or integrated support catheter (ISC) and microwire (MW); and, aspiration through the AC to effect suction on the blood clot with the distal tip immediately proximal to the blood clot.

In another aspect, the invention provides an integrated support and cooling catheter (ISCC) for assisting advancement of a D2BA catheter, the ISCC and enabling a cooling solution to be flowed through the ISCC after aspiration of a clot through the D2BA, the ISCC comprising a catheter having a tapered distal zone for supporting the distal tip of the D2BA during advancement through tortuous sections of a patient's cerebral vasculature and an insulated proximal zone enabling a cooling solution to introduced to a proximal end of the ISCC at 1-3° C. and wherein the cooling solution exits the ISCC at 2-8° C.

BRIEF DESCRIPTION OF THE DRAWINGS

The invention is described with reference to the drawings in which.

DETAILED DESCRIPTION OF THE INVENTION

Rationale

Figure 1A:
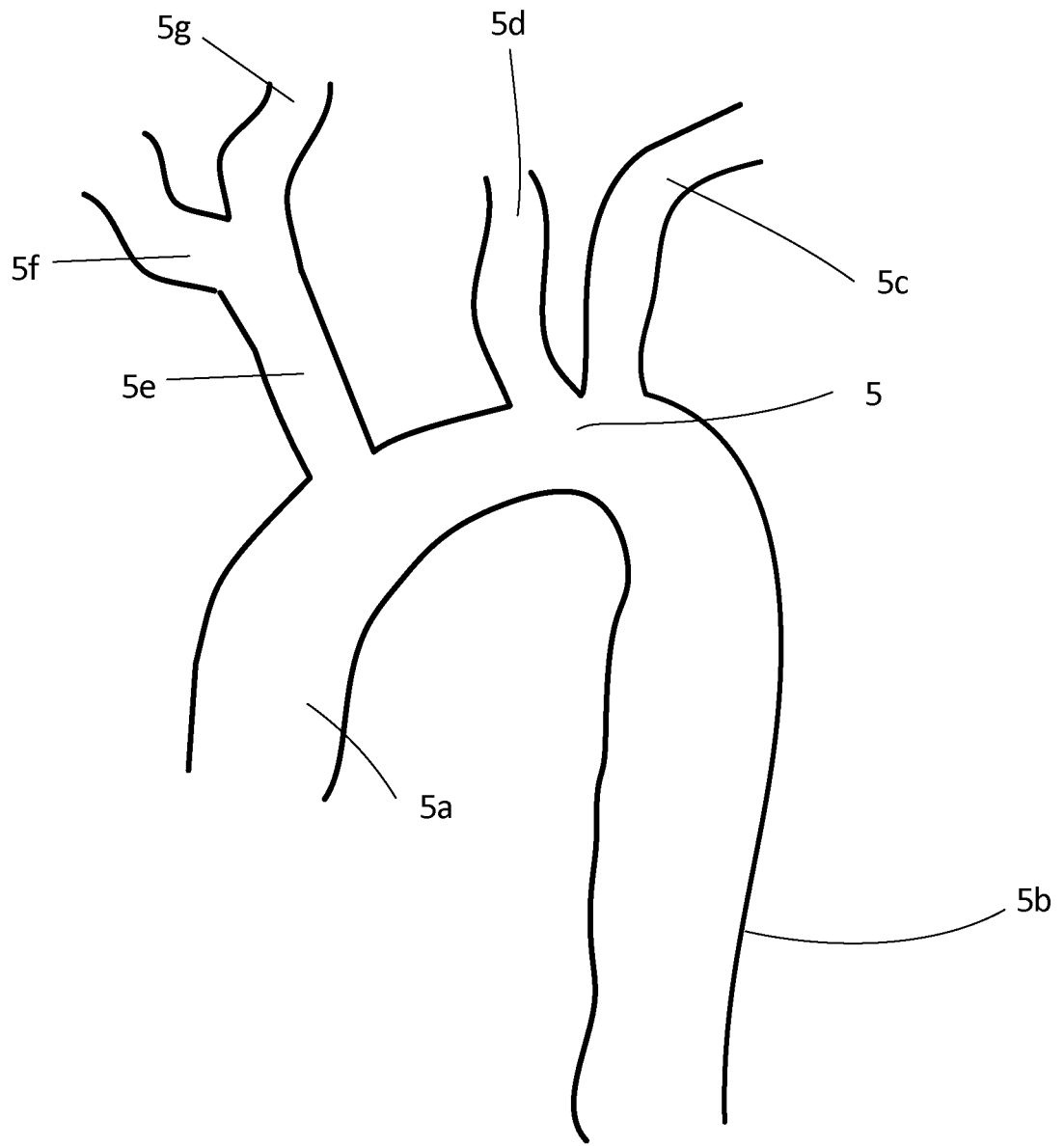
FIG. 1A is a sketch of a typical aortic arch and associated vessels in accordance with the prior art.

The inventor understood that aspirating blood clots from the cerebral arteries had limitations using current catheter designs and methods.

Terminology

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "distal", "proximal", "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a feature in the figures is inverted, elements described as "under" or "beneath" other elements or features would then be oriented "over" the other elements or features. Thus, the exemplary term "under" can encompass both an orientation of over and under. A feature may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present.

It will be understood that, although the terms "first", "second", etc. may be used herein to describe various elements, components, etc., these elements, components, etc. should not be limited by these terms. These terms are only used to distinguish one element, component, etc. from another element, component. Thus, a "first" element, or component discussed herein could also be termed a "second" element or component without departing from the teachings of the present invention. In addition, the sequence of operations (or steps) is not limited to the order presented in the claims or figures unless specifically indicated otherwise.

Structural parameters such as "axial stiffness", "radial compressibility", "axial compressibility" and "torquability" may be described as relating to various functional properties that a catheter in relation to a catheter's performance or behaviour in the human body during endovascular procedures as would be understood by those skilled in the art. That is, catheters as described herein, being sophisticated pieces of medical equipment that are used in complex medical procedures that use an assortment of other equipment (including the absence of various pieces of equipment) are more clearly and broadly defined in terms of their performance as opposed to specific definitions utilizing number ranges.

Other than described herein, or unless otherwise expressly specified, all of the numerical ranges, amounts, values and percentages, such as those for amounts of materials, elemental contents, times and temperatures, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Generally, outer diameters of catheters are referred to in French (FR) units whereas the inner diameters (IDs) of catheters are referred to in inches. When reference is made to the dimensions of a "sheath", French units are used to refer to an inner diameter.

Unless otherwise defined, all technical and scientific terms used herein have the same meaning as commonly understood by one of ordinary skill in the art to which this invention belongs.

Various aspects of the invention will now be described with reference to the figures. The invention may, however, be embodied in many different forms and should not be construed as limited to the embodiments set forth herein; rather, these embodiments are provided so that this disclosure will be thorough and complete, and will fully convey the scope of the invention to those skilled in the art. Moreover, the drawings are not necessarily drawn to scale and are intended to emphasize principles of operation rather than precise dimensions.

INTRODUCTION

Figure 1B:
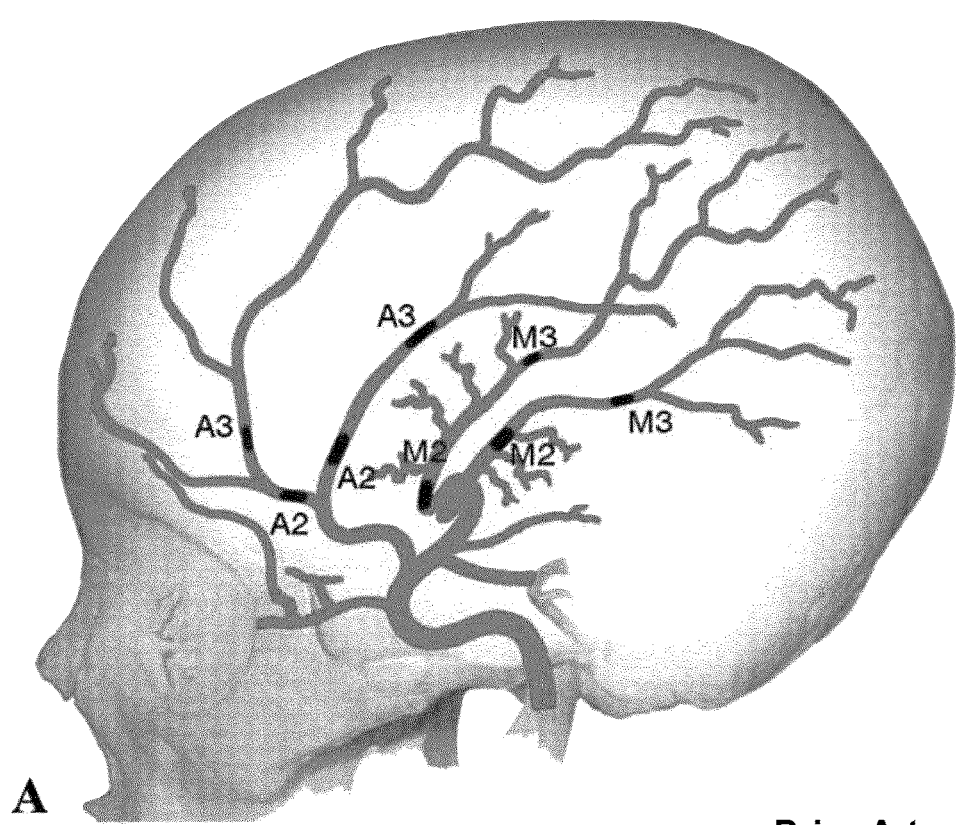
FIG. 1B is a schematic diagram showing medium vessel occlusion sites (MeVO) in accordance with the prior art. These are generally defined as sites in the anterior circulation including (A): proximal M2 segment, distal M2 segment, M3 segment, A2 segment, and A3 segment. MeVO sites in the posterior circulation are generally defined as the P2 segment or P3 segment (B).
Figure 1B:
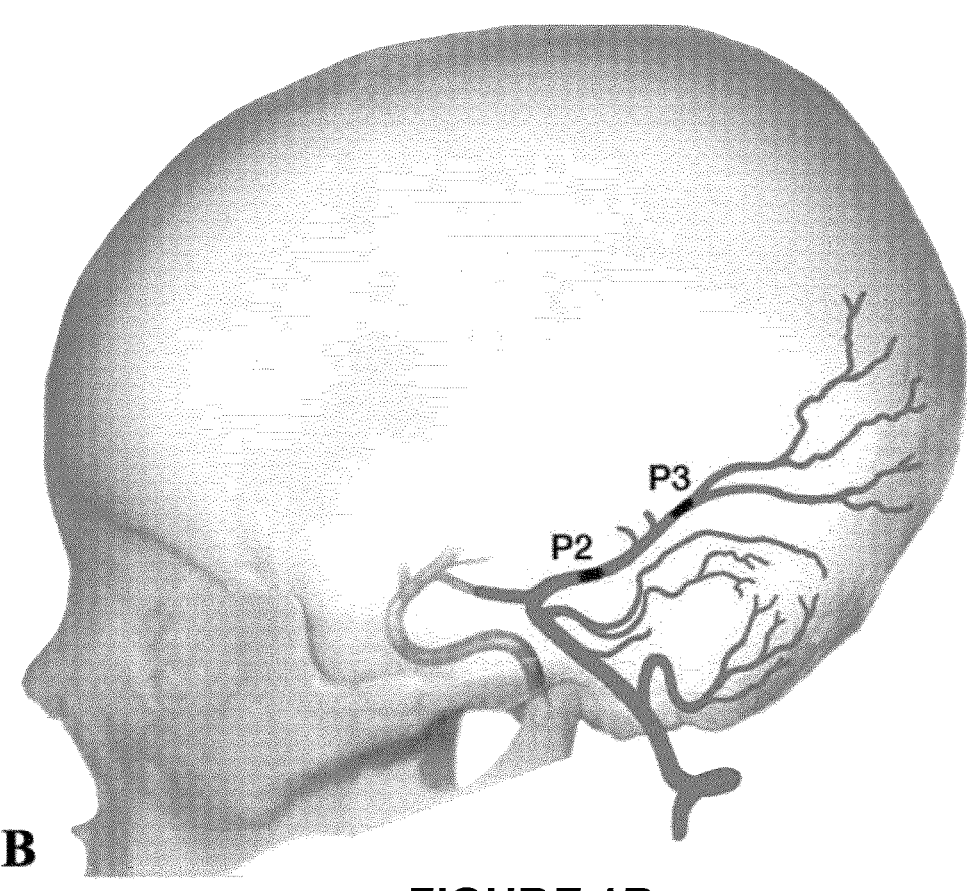
Figure 1C:
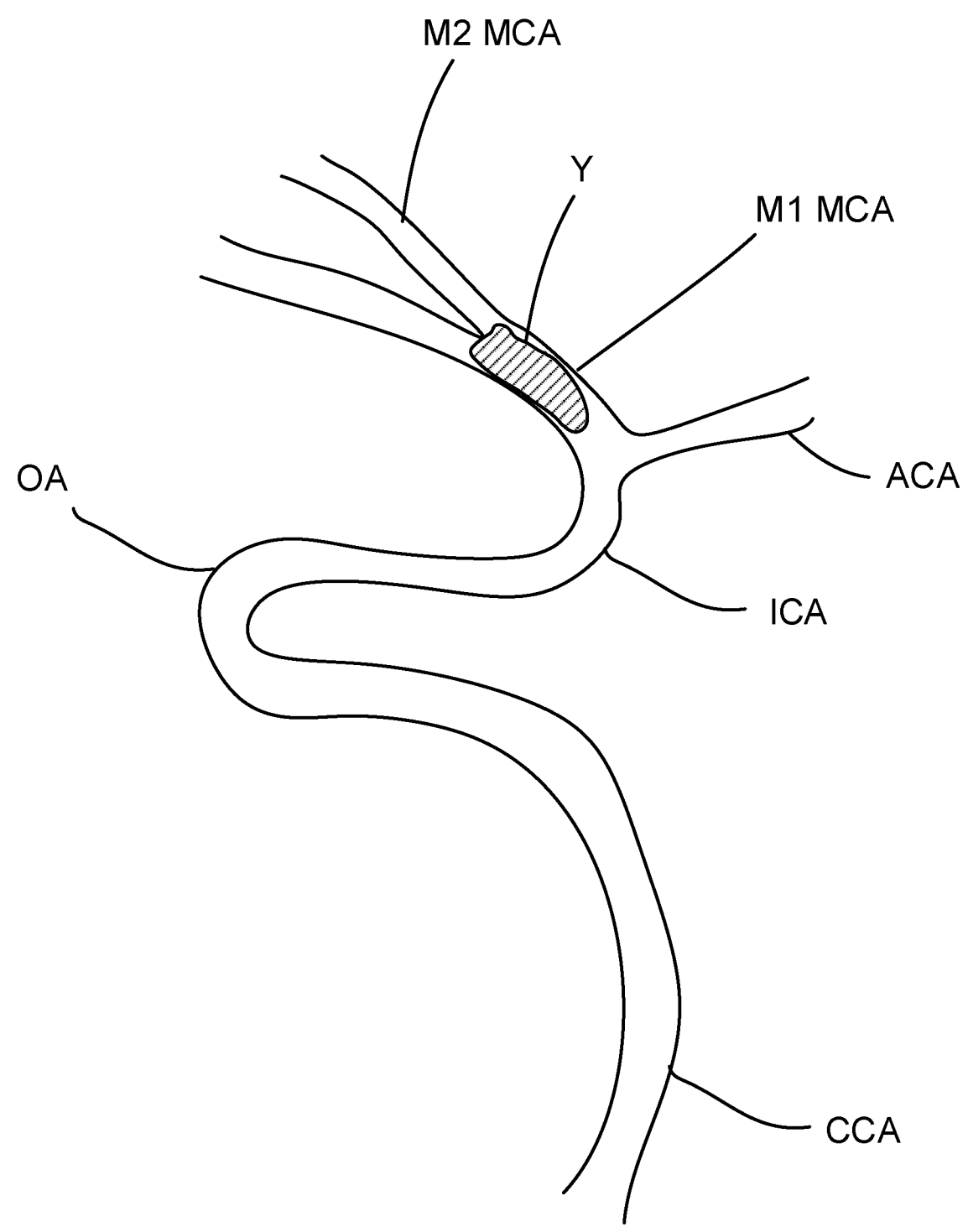
FIG. 1C is a schematic diagram of a clot Y lodged within the MCA at the M1 segment in accordance with the prior art.

FIG. 1A shows a typical aortic arch 5 and associated vasculature including the ascending aorta 5a, descending aorta 5b, left subclavian artery 5c, common carotid artery 5d, brachiocephalic artery 5e, right subclavian artery 5f and internal carotid artery 5g. FIG. 1B is a schematic diagram showing medium vessel occlusion sites (MeVO). These are generally defined as sites in the anterior circulation including (A): proximal M2 segments, distal M2 segments, M3 segments, A2 segments, and A3 segments. MeVO sites in the posterior circulation (B) are generally defined as the P2 segments or P3 segments. FIG. 10 is a schematic diagram of a clot lodged in the M1 segment of the MCA. Associated vessels include the common carotid artery (CCA), ophthalmic artery (OA), internal carotid artery (ICA), anterior cerebral artery (ACA) and middle cerebral artery (MCA) including M1 and M2 segments.

Figure 2A:
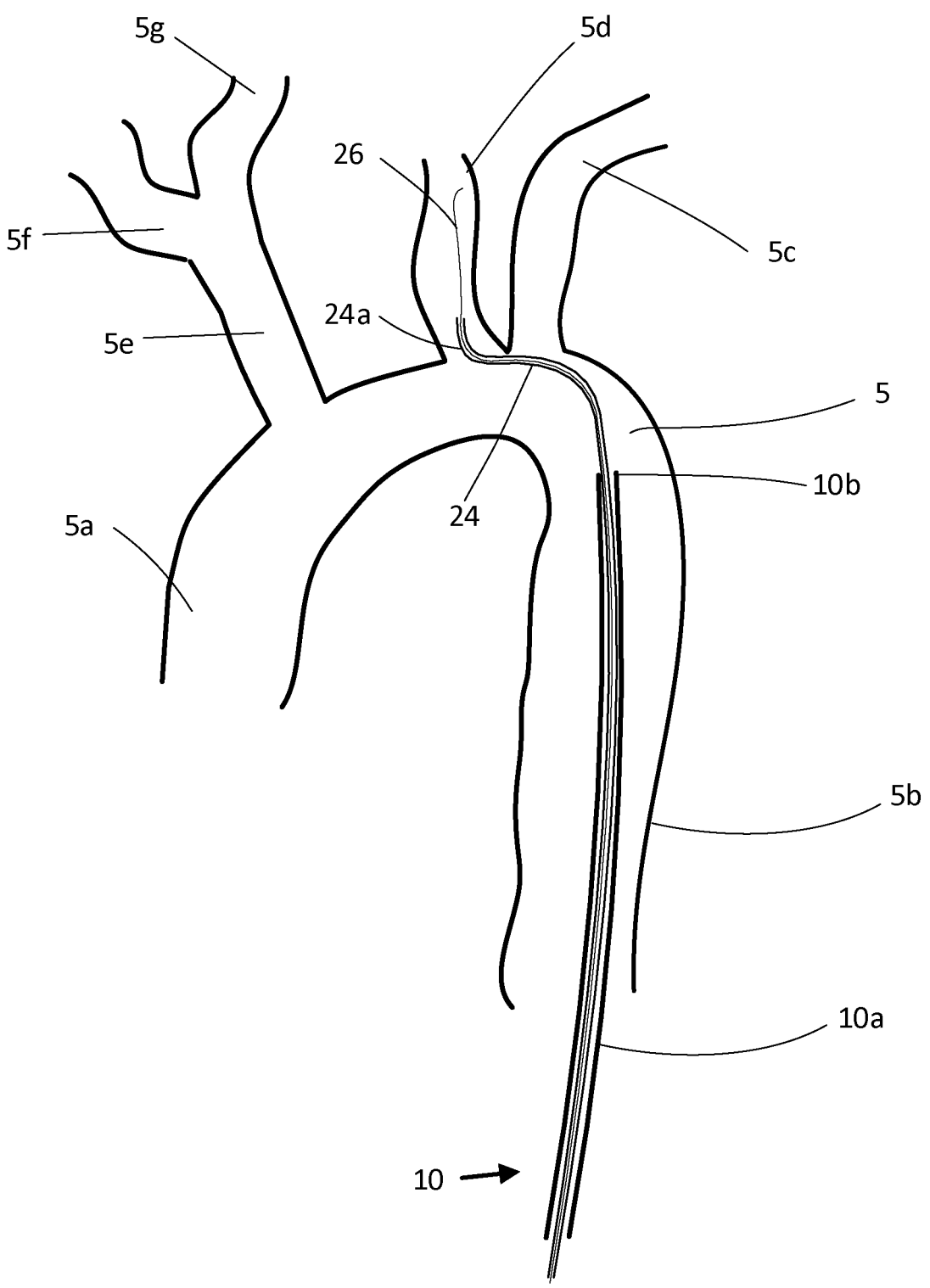
FIG. 2A is a schematic diagram showing advancement of a guide wire, diagnostic catheter and G2BA through the aortic arch and into the common carotid artery (CCA) in accordance with one embodiment of the invention.
Figure 2B:
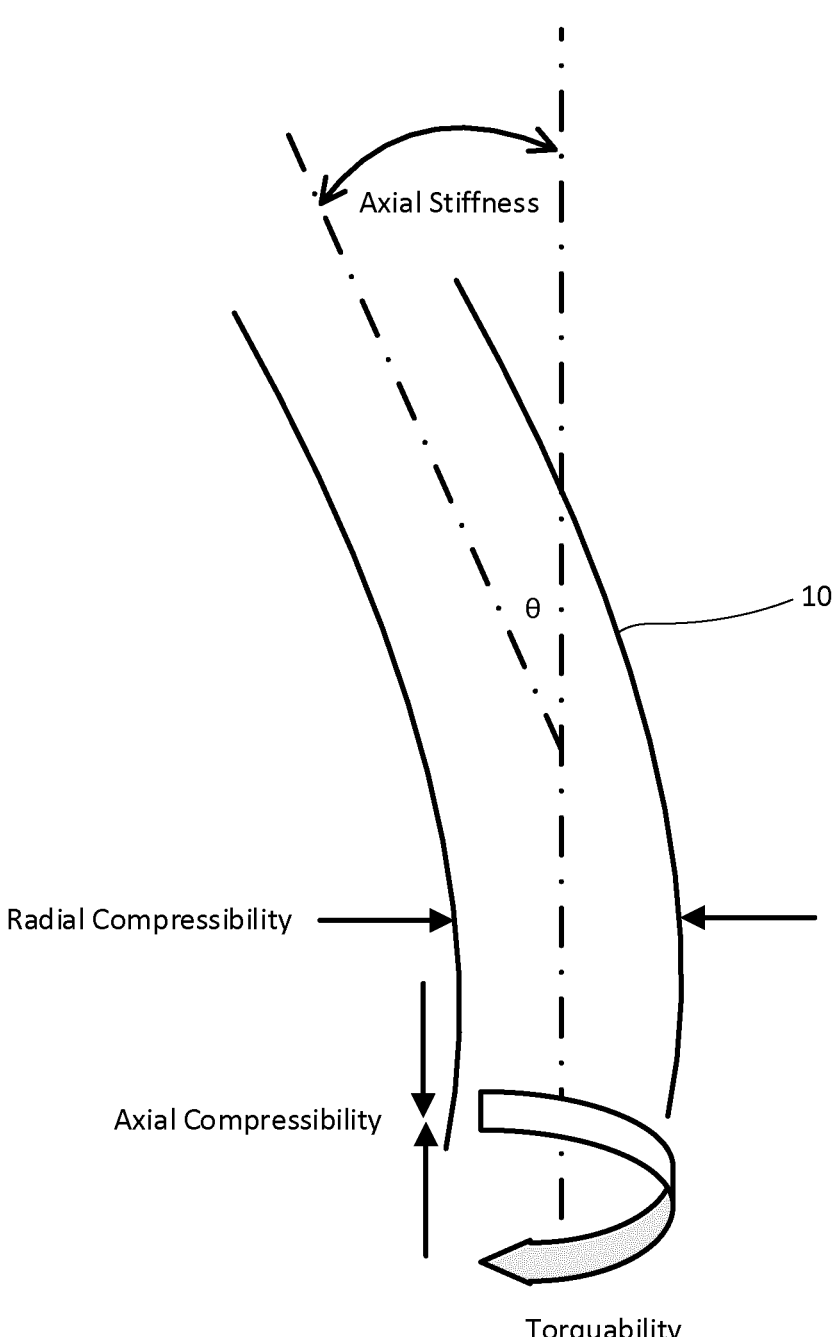
FIG. 2B is a schematic diagram showing features of a G2BA in accordance with the invention including structural parameters of axial stiffness, radial compressibility, axial compressibility and torquability.
Figure 3:
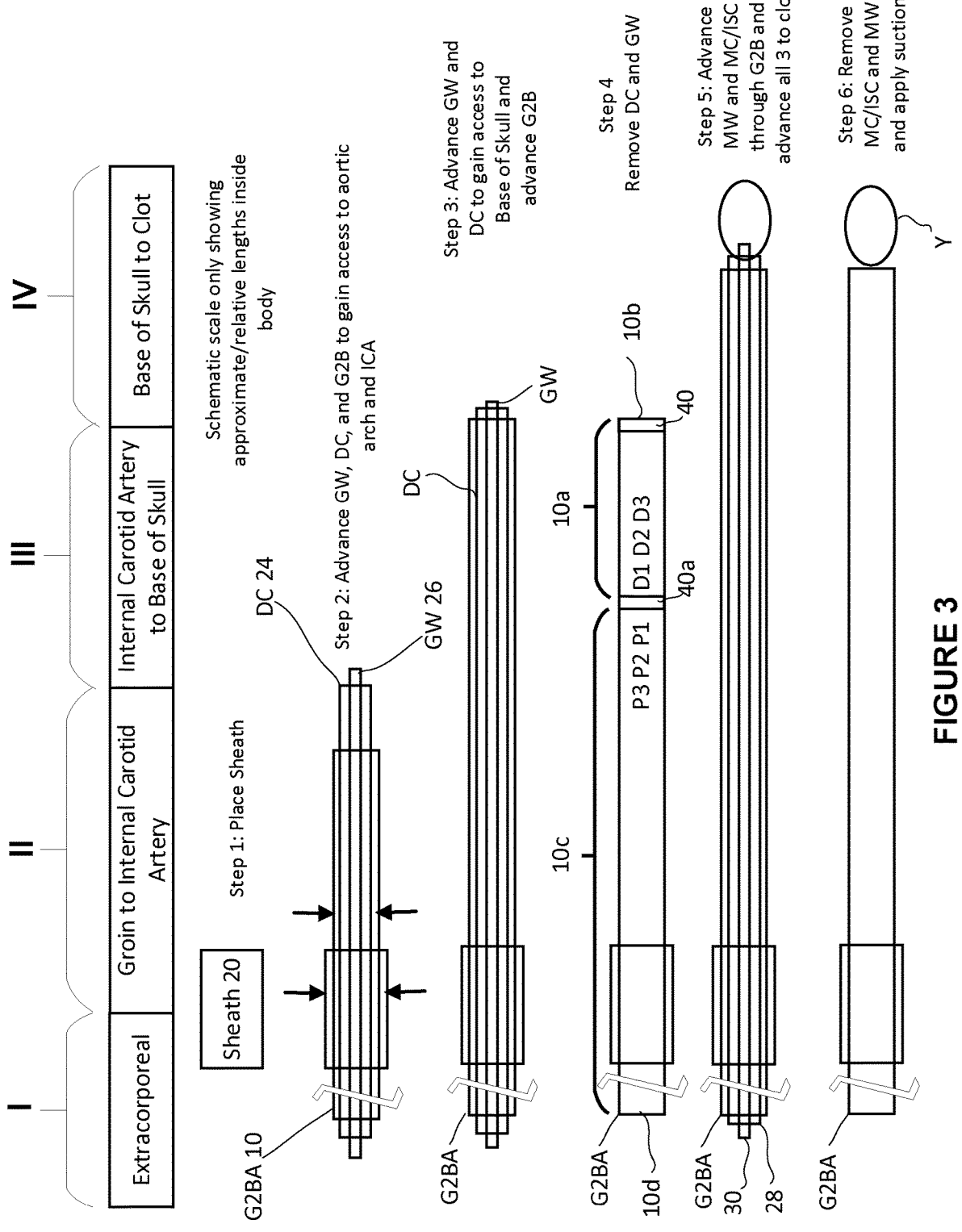
FIG. 3 is a schematic diagram showing the steps of a procedure in accordance with one embodiment of the invention to position a G2BA catheter within the cerebral arteries of a patient.

In accordance with the invention, with reference to FIGS. 2A and 3, large size aspiration (LSA) catheters 10 are described having 1) a distal zone 10*a* having a distal end 10*b* that can be positioned adjacent a typical clot within particular zones of the cerebral vasculature including level 2 segments of the middle cerebral artery and basilar artery (or higher) (collectively the "target levels") 2) a proximal zone 10*c* having a proximal end 10*d* where the LSA catheter does not require external (eg. via a guide catheter (GC) or balloon guide catheter (BGC)) support when it is being advanced through the aortic arch and into the cervical arteries and 3) outside diameters (ODs) greater than 6 French and less than or equal to 10 French.

In the context of this description, in various embodiments, the LSA catheter is referred to as a groin to brain aspiration catheter (G2BA) which refers to the most common access point (i.e. the groin) for conducting cerebral endovascular procedures. However, the LSA catheter may also be referred to as a distal entry point (DEP) to brain catheter (D2BA), which contemplates distal entry points including both the femoral artery (groin) and the radial artery. That is, it is understood that other entry points for cerebral endovascular procedures besides the groin are contemplated in accordance with the invention. Generally, as noted below, the length dimensions of the proximal zone of a D2BA are adjusted based on the DEP having consideration to the respective distance from a groin entry point vs. a radial artery entry point. As such, reference to LSA, G2BA and D2BA catheters are used within the description.

Generally, the G2BA catheter is defined as a catheter useful to conduct endovascular procedures in the brain having a larger OD (7-10F) and a corresponding larger lumen (internal diameter) extending from the proximal end 10*d* to the distal end 10*b* wherein the ID of the lumen is in the range of 0.066" to 0.105" (preferably 0.072" to 0.105" and more preferably 0.078" to 0.105" determined on basis of the intended target level).

In general, the outer diameter of the G2BA catheter at its distal end is expected to closely match the lumen diameter of the target vessel and where the inner diameter of the G2BA is the largest possible (i.e having a minimized wall thickness) that provides the necessary rigidity to conduct an aspiration procedure as described herein.

As such, at one level the invention seeks to enhance clot capture by aspiration by minimizing the diameter difference between the clot and G2BA catheter. In this regard, it is recognized that the ID of the G2BA catheter cannot equal the vessel lumen (due to the catheter wall thickness) but that clot capture can be substantially improved by minimizing this difference. Moreover, it is also recognized that a clot usually has some degree of compressibility and that the placement of a catheter having an OD substantially the same as a target vessel results in the catheter being effectively wedged in the target vessel which improves suction pressure to the clot as will be described in greater detail. It is also recognized that a larger G2BA lumen enables a higher aspiration force to be applied without damage to the vessel intima.

Importantly, in the past, advancement of larger size aspiration catheters within the brain was often not possible as aspiration catheters require larger guide catheters to be advanced into the neck to externally support the aspiration catheters when being advanced. The use of external guide catheters reduces the effective size of aspiration catheters that can be advanced through the guide catheters. In addition, heretobefore, aspiration catheters could not be advanced over DCs/GW due to the relative distal stiffness of such catheters. Moreover, in the past, it has been difficult to advance aspiration catheters through certain vessels (eg. the ophthalmic artery) due to the tortuosity of such vessels and their relative distal tip stiffness. While U.S. Pat. No. 10,456, 552 teaches that advancement of certain catheters through tortuous sections of the cerebral vasculature can be improved utilizing internal support catheters (ISCs), there are limits given the structure of an aspiration catheter.

As shown in Table 3, the G2BA is designed in different lengths and outside diameters (i.e. French sizes; referred to as "catheter size") that enable access to particular levels of the brain. These parameters are identified and discussed in Table 3.

TABLE 3

| G2BA Features and Properties | | |
|---|---|---|
| Feature | Value | Discussion |
| Overall Length | Approximately 120-140 cm | The overall length of a G2BA will be determined by the desired brain location where the the physician wishes to place the distal tip of a G2BA. That is, smaller French size catheters will generally be longer and larger French size catheters will be shorter reflecting the total distance from extracorporeal access point to the target vessel in the brain. For groin access catheters this range will typically be 120-140 cm. Radial artery access catheters will be proportionally shorter. |
| | | Distal Tip Zone |
| Length | Approximately 20 cm Range 18-30 cm | The length of the distal tip zone will also be determined by the desired brain location where the the physician wishes to place the distal tip of a G2BA. Similarly, a shorter distal tip region will be incorporated into a G2BA having a larger French size whereas longer distal tip regions will be incorporated into a G2BA having a smaller French size. |

TABLE 3-continued

| G2BA Features and Properties | | |
|---|---|---|
| Feature | Value | Discussion |
| End Anatomical Position | Cerebral arteries (Anterior and Posterior circulations) Level 2 segments max | The overall length of the G2BA and distal tip zone length are determined by different end anatomical positions. Generally, the furthest level of effectiveness of a primary G2BA will be Level 2 segments of the middle cerebral artery and the basilar artery. Anatomical variants that lead to very prominent Anterior cerebral artery, Posterior cerebral artery, Persistent Trigeminal artery may also be accessed using a G2BA. For example, a 7F G2BA is designed to reach Level 2 segments (M2 segment of the MCA), an 8F G2BA is designed to reach the mid-Level 1 segments (distal M1 segment of the MCA), a 9F G2BA is designed to reach Level 1 segments (proximal M1 segment of MCA) and a 10F G2BA is designed to reach the distal ICA level (or equivalent). Secondary G2BAs may access deeper regions including Level 3 segments or equivalents. |
| Axial Stiffness | Soft | The axial stiffness of the distal tip region is sufficiently pliable to enable movement through cerebral arteries to the desired level and to be able to ride over a guide wire and diagnostic catheter and/or ISC and MW positioned between a DEP and cervical arteries without causing prolapse of the DC and GW. |
| Distal Tip Outside Diameter | Preferably 6-10 F | The distal tip OD corresponds to the G2BA catheter size, namely 6 F-10 F. |
| Distal Tip Inside Diameter | Preferred ID Range 0.053-0.105 inches | For each catheter size, the distal tip inside diameter will be maximized whilst ensuring functionality as described. That is, that is distal tip wall thickness is ideally minimized whilst ensuring the aspiration and deployment properties remain. In practical terms, catheters may have a wall thickness in the range of 0.009". For a 7 F catheter having a wall thickness of approximately 1 F or 0.009" and an OD of 0.092", the distal tip ID is approximately 0.074". Other IDs are shown in Table 4. |
| Proximal Diameter | same or minimally larger than distal diameter | The G2BA will generally have a consistent OD along its length; however some tapering is not excluded. Tapering may allow for a minimally larger distal diameter. |
| Tip Edge | rounded/ atraumatic/ radio-opaque/ oblique angle or bevelled tip | The distal tip edge will be rounded/atraumatic to allow contact with the vessel intima without damaging the intima. The tip will be radio-opaque to assist the physician in correctly positioning the G2BA. The radio-opaque portion will typically be a ring structure incorporated into the distal tip. The distal tip edge may have an oblique/bevelled end to facilitate clot capture as described below. |
| Opening Radial rigidity | Semi-Rigid | Enables retrograde flow and recovery of clot. The radial rigidity will be sufficient to enable retrograde flow and clot capture without collapse. The radial rigidity is balanced with axial rigidity/flexibility. |
| Axial rigidity/ flexibility/ compressibility /torquability. | | The G2BA axial rigidity is sufficient to enable distal movement of the G2BA over an ISC, MC, MW and/or a DC without external support. The G2BA axial flexibility is sufficient to enable distal movement around curves (potentially in conjunction with an ISC to assist as explained herein). The G2BA axial compressibility is sufficiently rigid to prevent axial buckling of the G2BA under deployment conditions. The G2BA may be torquable along its length. |
| | | Proximal Zone |
| Length | Approximately 100 cm for a G2BA (90-110 cm) | The proximal zone length is determined having consideration to the OD size of the G2BA, the DEP and end anatomical position. |
| End Anatomical Position | Extracorporeal to distal cervical arteries | The end anatomical position of the proximal zone region is variable and for a given G2BA will generally be determined by the length of the distal tip region. In other words, the G2BA is primariliy designed by the length of distal tip region such that the end anatomical position of the proximal zone will be in the region of the base of the skull during deployment with a length sufficient to extend to the DEP and outside the body. |

TABLE 3-continued

| G2BA Features and Properties | | |
|---|---|---|
| Feature | Value | Discussion |
| Distal Junction Internal Diameter | same or minimally larger than distal zone | The G2BA will generally have a consistent ID along its length. The G2BA will generally not be characterized by a "hard" transition between the distal/proximal zones but rather has a zone of transition having a range of axial stiffness (i.e. flexibility) values throughout this zone. |
| Proximal External Diameter | 7-10 F | The G2BA will generally have a consistent OD along its length. |
| Radial Rigidity | May be stiffer than distal | The G2BA radial rigidity in the proximal zone is the same or higher than the radial rigidity of the distal tip region. |
| Axial stiffness/ rigidity/ flexibility Axial compressibility Axial torquability | | The G2BA axial stiffness/rigidity/flexibility in the proximal zone is the same or higher than the axial stiffness/rigidity/flexibility of the distal tip region and sufficient to enable distal movement of the G2BA over an ISC, MC, a MW and/or a DC without external support. The G2BA axial stiffness/rigidity/flexibility in the proximal zone is the same or higher than the axial flexibility of the distal tip region and sufficient to enable distal movement around curves such as through the aortic arch. The G2BA axial compressibility in the proximal zone is the same or higher than the axial compressibility of the distal tip region and sufficiently rigid to prevent axial buckling of the G2BA under deployment conditions. The G2BA may be torquable along its length. |

Importantly, it is understood that the transition between the proximal and distal zones is preferably not abrupt and that a transition zone may include a number of sub-zones that provide a transition between the properties of the proximal and distal zones. That is, the axial stiffness of the distal zone may progressively increase in the proximal direction such that the physical properties of the G2BA have sub-zones where the properties are consistent over a 4-8+cm segment and then step to a different sub-zone with different properties. For the proximal zone, these are shown representatively as P1, P2 and P3 (where stiffness may increase from P1-P3) and as D1, D2 and D3 (where stiffness may decrease from D1-D3) for the distal zone in FIG. 3. As such, the point of transition between the distal zone and the proximal zone is generally considered to be a measured distance from the distal tip (for a particular target level) where the transition point is the high cervical arteries. In some embodiments, a specific radio opaque marker 40a may be incorporated into the transition point to assist the physician in visualizing the location of the transition point as well as at a radio-opaque distal tip marker 40.

TABLE 4

| Typical OD and ID sizes of Catheters | | | |
|---|---|---|---|
| French | Typical Wall Thickness (inches) | Typical ID (inches) | OD (inches) |
| 7 | 0.009-0.013 | 0.066 | 0.092 |
| 8 | 0.009-0.013 | 0.079 | 0.105 |
| 9 | 0.009-0.013 | 0.092 | 0.118 |
| 10 | 0.009-0.013 | 0.105 | 0.131 |

The relative size of the G2BA catheter and the ability to deploy the G2BA to a level where the distal tip is substantially engaged with the ID of the vessel and in close proximity to a clot provides numerous advantages over past systems and specifically improves the time to access and the ability to capture clots via aspiration.

The G2BA catheter obviates the need for a GC or BGC by preventing (or substantially stopping) antegrade flow during a procedure and the attendant risk of micro-emboli being carried away. That is, the effective size of the G2BA relative to the ID of the vessel can substantially prevent antegrade flow after the G2BA catheter has been positioned due to gentle wedging of the distal tip within the target vessels.

G2BA Construction

Catheters used to access regions of the brain are constructed using a variety of techniques to give the catheter the desired performance properties including pushability, torquability, trackability and stiffness. Generally, a catheter may be constructed from engineered polymers including polyurethanes, nylons, silicone rubber, polyethylene terephthalate (PET), latex, thermoplastic elastomers and polyimides. Microfilaments of polymers and metals may be incorporated.

Typically, catheters are manufactured from an assembly of smaller sections of various formulations of the polymers that have been extruded, thermoformed and/or thermoset using a wide range of techniques including casting and/or assembly over a mandrel. Each formulation has been engineered to include different properties; hence, different sub-zones may have for example slightly different stiffness properties along the length of either the proximal or distal zones as noted above.

Deployment Methods and Use

Figure 3A:
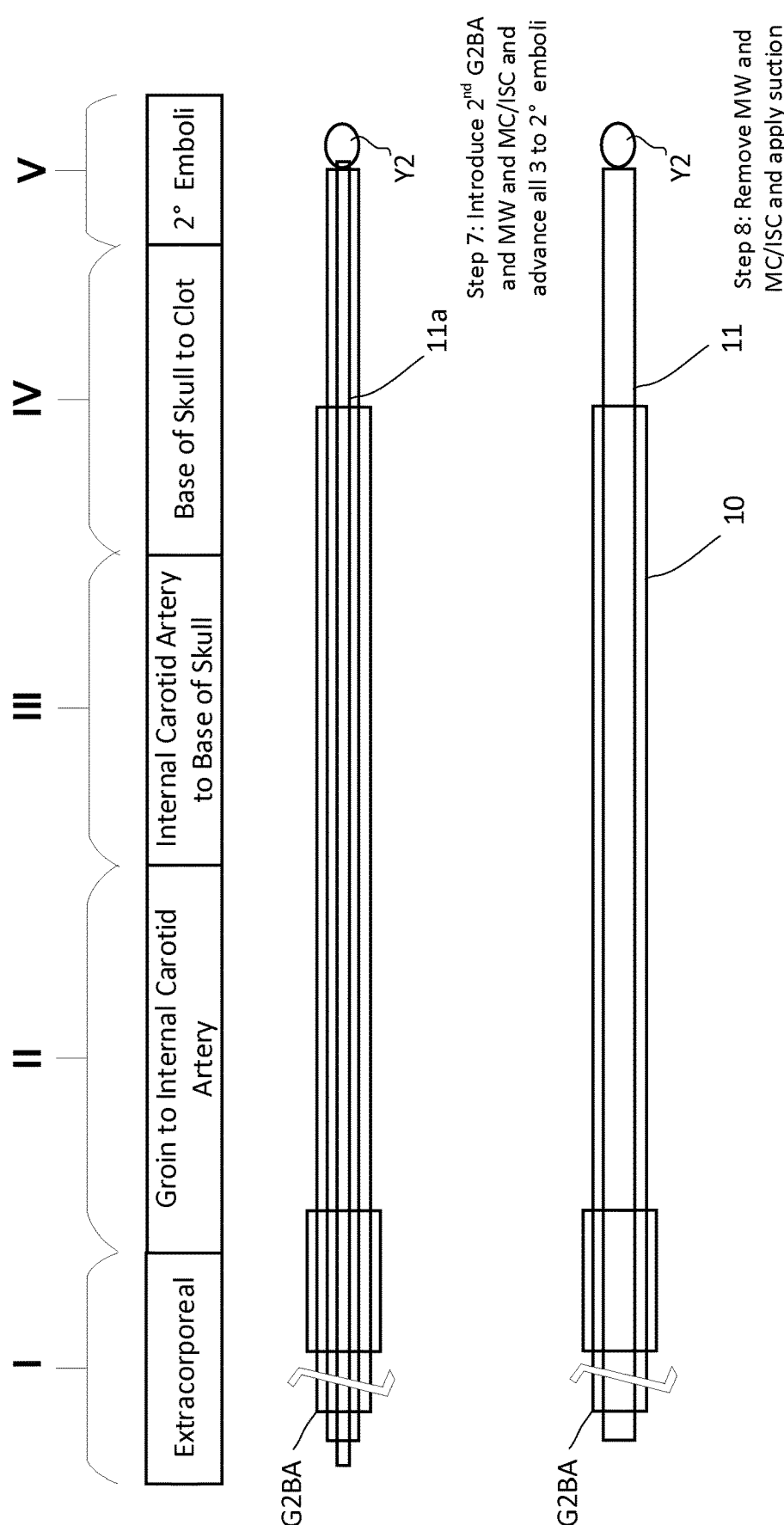
FIG. 3A is a schematic diagram showing additional steps of a procedure in accordance with one embodiment of the invention to position a G2BA catheter at a higher level within the cerebral arteries of a patient.

In accordance with a method of the invention, procedures for introducing a G2BA catheter are described (referred to as "the G2BA method") with reference to FIGS. 2A, 3 and 3A. For the purposes of description, FIGS. 2A, 3 and 3A assume access from the femoral artery and desired access to the M1 segment through the ICA. It should also be noted that the lengths of each piece of equipment in FIGS. 3 and 3A are not specifically drawn to scale and specifically, for clarity, sections of each piece of equipment outside the body are not drawn to show a consistent overall length in each of the steps outlined below.

Initially, after arterial puncture, a sheath 20 is deployed (Step 1). A femoral artery sheath will have a maximum ID of about 12F (typically 9-10F). Access through the radial or brachial artery will utilize a sheath having a maximum ID of about 7F-8F.

Thereafter or concurrently, an assembly of a G2BA 10, a diagnostic catheter (DC) 24 with tip 24a and guide wire (GW) 26 (typically 0.035") is assembled and progressively introduced into the sheath (Step 2) and advanced to the aortic arch. The chosen assembly of G2BA, DC and GW will be based on the location of the clot together with the physician's assessment of the aortic arch access vessel and the patient's aortic arch anatomy/variability. That is, in planning the procedure, the physician will have determined where the clot is located and how access to the clot is to be achieved. In this example, if the clot is at the M1 level requiring access through the common carotid artery (CCA) and ICA, an 8F G2BA may be selected in combination with a preferred DC for accessing the CCA. Alternatively, if the clot is located at the P1 level of the basilar system requiring access through the right subclavian, a smaller (eg. 7F) G2BA and different DC may be selected and assembled.

As the GW and DC are advanced to the aortic arch, the distal tip 10b of the G2BA will also be advanced and held in a position typically no more than 20 cm behind.

The DC and GW are manipulated to gain access to the desired cervical artery (Step 2). The GW is generally held at substantially the same position as the DC during the steps where access to the cervical artery is being obtained. During this step, the DC and GW are torqued, pushed and/or pulled in order to hook the tip of the DC into the desired vessel. When the DC/GW are in the desired vessel, by a combination of advancing the GW and DC, the two can be advanced to the base of the skull (Step 3). In the presence of severe tortuousity or stenosis or occlusion of the origin of the internal carotid artery (ICA) for example, initial access to the external carotid artery (ECA) could be obtained. In certain situations, the use of a second "buddy wire", that is a second GW may also be deployed to assist the physician in providing support to the system.

With the GW and DC being held at roughly the base of the skull, the G2BA is also advanced over the DC/GW such that the G2BA follows the DC and GW until the distal tip of the G2BA is adjacent the distal tip of the DC and GW (Step 3). The soft distal tip and the lack of a pre-determined shape of the G2BA makes it conducive to follow the DC and GW. At this point, the soft distal tip is fully within the cervical arteries and the stiffer proximal portion of the G2BA is within the cervical arteries and approximately 10 cm (8-12 cm) past the aortic arch. The GW and DC would typically not be advanced past the base of the skull and would be removed (Step 4).

Importantly, with the stiffer portion of the G2BA in the cervical arteries, and the removal of the DC and GW (step 4), the risk of prolapse of the G2BA into the ascending aorta is substantially eliminated when further equipment is introduced into the G2BA (Step 5).

Figure 4:
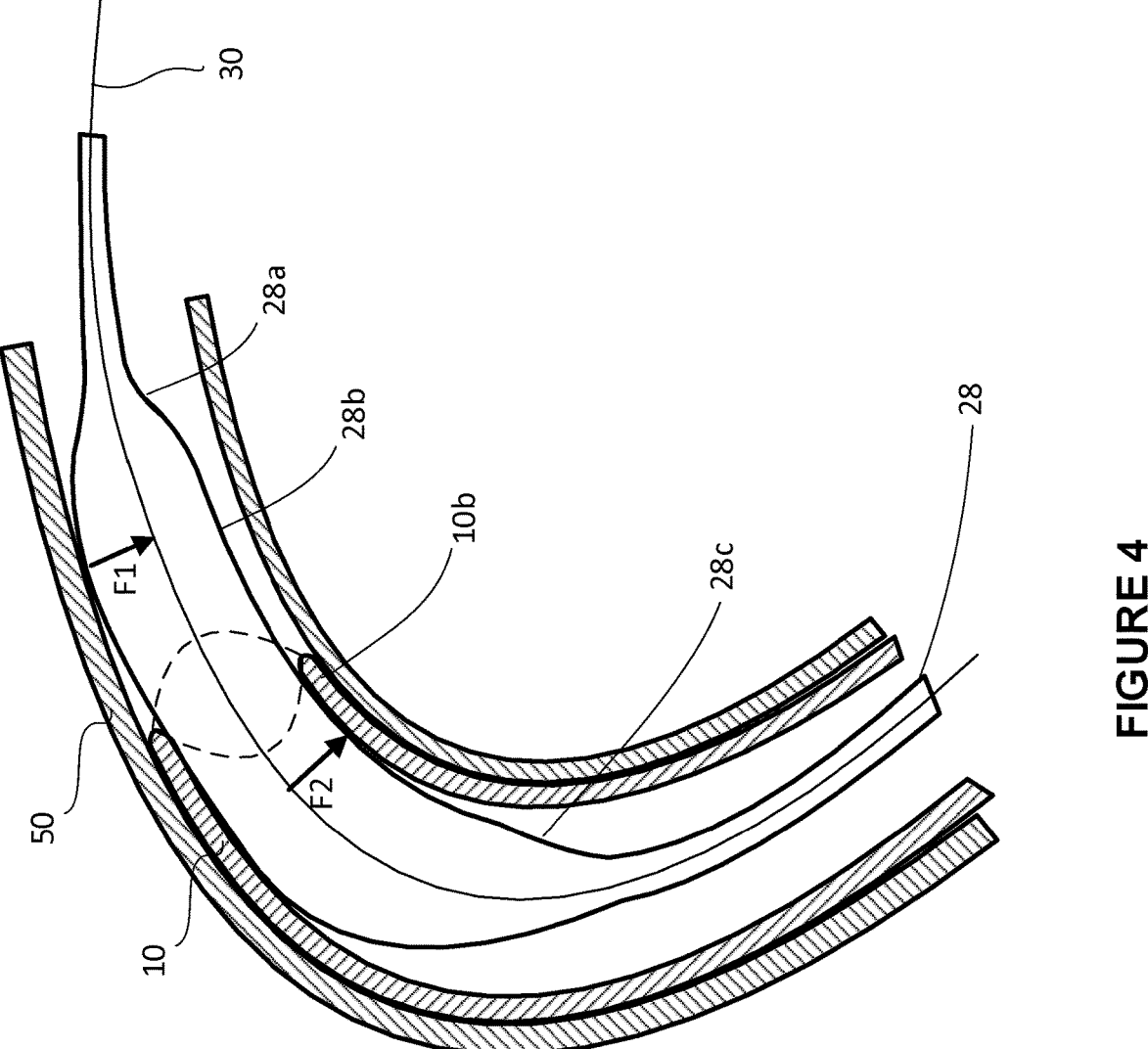
FIG. 4 is a schematic diagram showing the use of an integrated support catheter (ISC) is an assisting a G2BA catheter through a tortuous section of the cerebral vaculature in a accordance with one embodiment of the invention.

In Step 5, a microcatheter (MC) or an integrated support catheter (ISC) 28 and a microwire (MW) 30 are introduced and are advanced to the clot Y. When the clot is reached with the MC or ISC and MW, the G2BA 10 is advanced over the MC or ISC to the face of the clot. For reasons explained below, it is preferred that an ISC is used. As shown in FIG. 4, ISCs 28 are characterized as having a distal taper 28a, straight section 28b and proximal taper 28c (in various embodiments, an ISC may not have a proximal taper and the straight section 28b may extend along the entire proximal length of the ISC) that supports and otherwise provides an effective transition between the distal end 10b of a catheter and a microcatheter to form a smooth extension of the distal end 10b of a catheter. That is, an ISC fills the distal end of the G2BA catheter and provides a smooth extension to a catheter particularly as the catheter assembly is moved through tight curved areas of the vasculature 50. By extending and engaging with the vessel wall 50, the vessel wall exerts a force F1 against the ISC that is transmitted through the ISC such that the ISC exerts a force F2 against the distal tip 10b of the G2BA that then aligns the G2BA within the vessel 50 allowing the G2BA to be more effectively pushed through the vessel. Thus, through selective manipulation of each of the G2BA, ISC and MW, the physician can advance the G2BA past the tortuous section.

An ISC is not required in that a physician may believe that it will be unlikely that the G2BA will get stuck but in most cases it is preferable to introduce an ISC instead of a MC in anticipation of the G2BA potentially getting stuck.

Figure 4A:
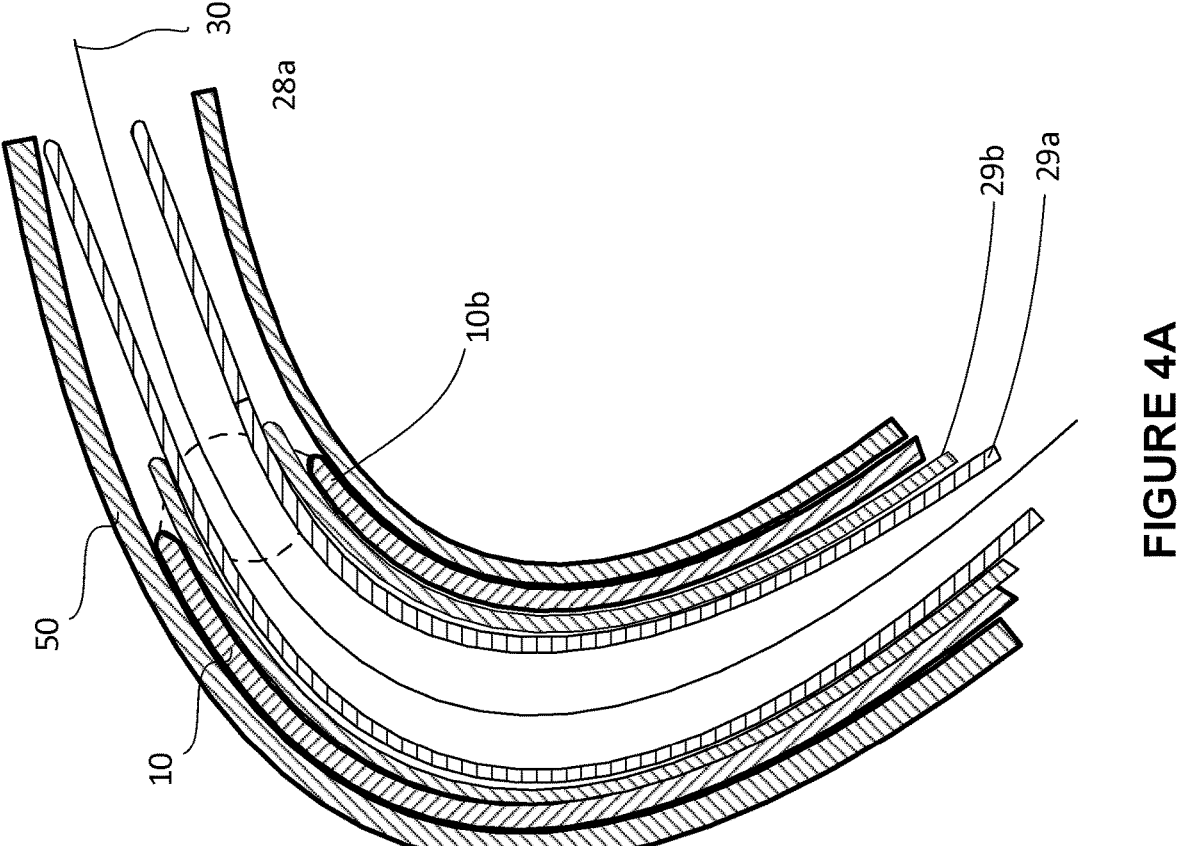
FIG. 4A is a schematic diagram showing the use of two microcatheters as an integrated support catheter (ISC) is an assisting a G2BA catheter through a tortuous section of the cerebral vaculature in a accordance with one embodiment of the invention.

Further still, as shown in FIG. 4A, an alternative may be for the physician to use two or more microcatheters (29a, 29b) to ease the G2BA around a tight curve. In this case, each MC may be selectively advanced short distances from the distal tip of the G2BA to provide the alignment to prevent the G2BA from becoming stuck.

The MC/ISC and MW are pushed forward to extend from the distal tip of the G2BA. The MC or ISC and MW and G2BA are progressively advanced to the clot through sequential manipulation of each.

Importantly, it should again be noted that in comparison to past aspiration catheters, the OD of the G2BA is larger and a comparatively larger distal tip has been advanced further.

Figure 5A:
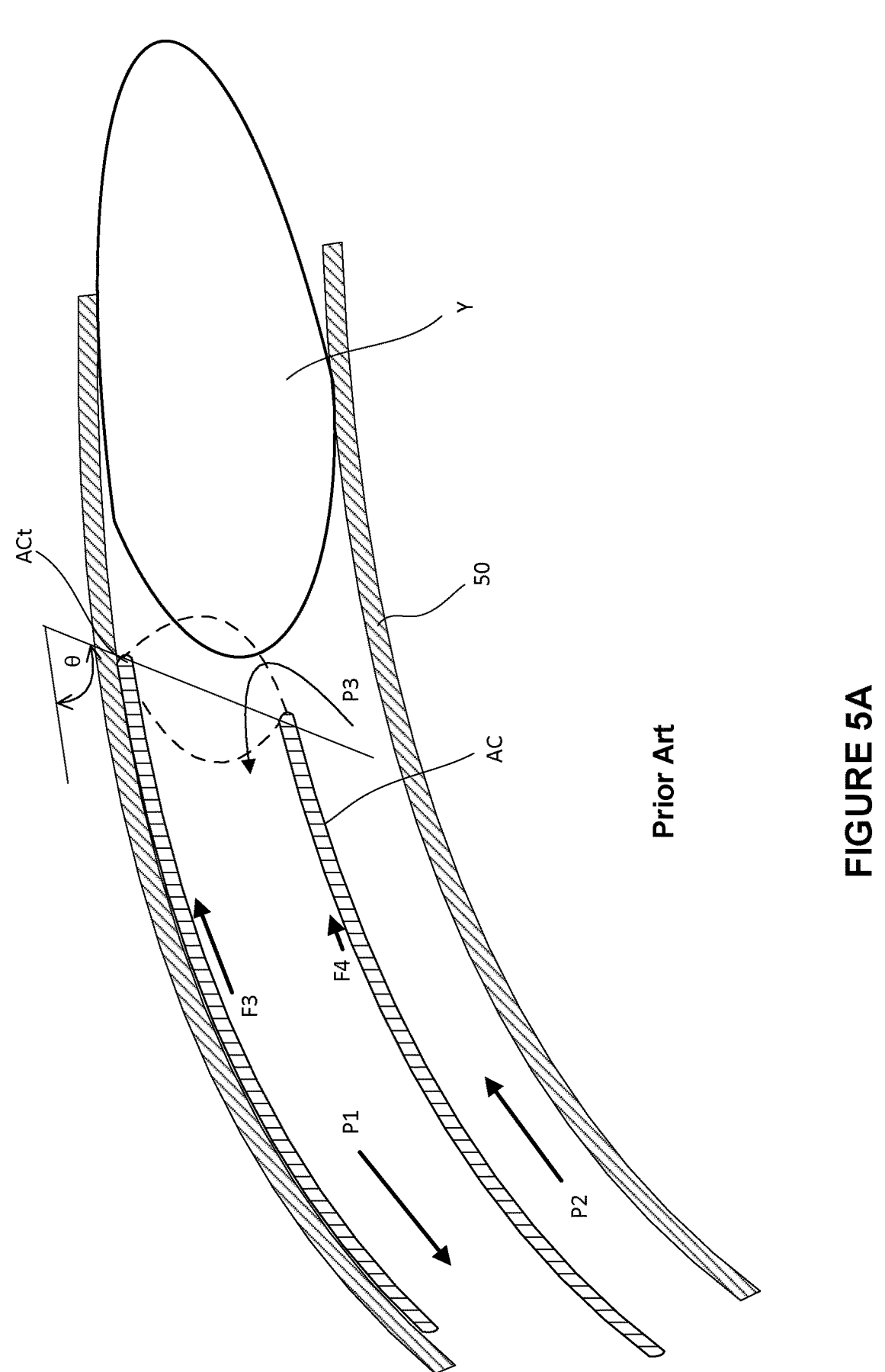
FIG. 5A is a schematic diagram showing the potential engagement of an aspiration catheter and clot in accordance with the prior art.
Figure 5B:
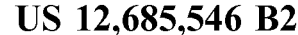
FIG. 5B is a schematic diagram showing the potential engagement of an aspiration catheter and clot in accordance with the prior art after suction has been applied.
Figure 5C:
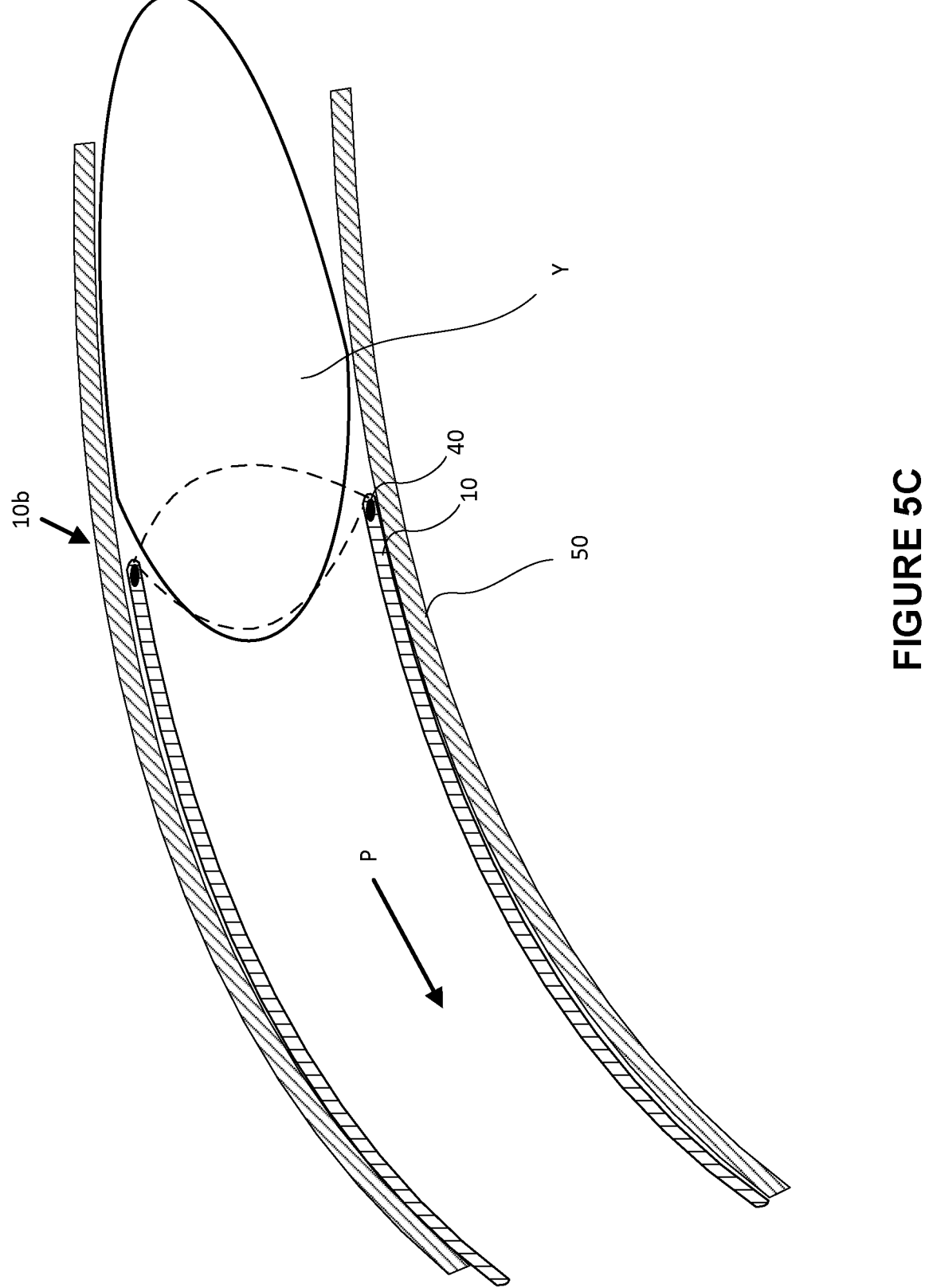
FIG. 5C is a schematic diagram showing the potential engagement of a G2BA catheter and clot in accordance with one embodiment of the invention after suction has been applied.

The larger distal tip diameter generally means that the G2BA will essentially occlude the vessel it is in and hence, due to a support pressure from the vessel walls, it will be more likely that the distal tip of the G2BA is aligned perpendicularly to the vessel as shown in FIG. 5C as opposed to be marginally deflected as shown in FIG. 5A. That is, as shown in FIG. 5A, an AC in accordance with the prior art that is smaller than the vessel may have unequal push forces being applied along inside and outside edges of the catheter such that an outside edge where there is a greater force F3 has extended one side of the distal tip ACt further through the vessel as compared to an inside edge and force F4 resulting in a deflection of the distal tip to an angle θ. As shown in FIG. 5A, if the distal tip ACt is not aligned, applying an aspiriation pressure P1 can result in less effective pressure being applied as blood may flow back into the catheter as shown by P2 and P3.

Furthermore, techniques of improving clot capture with a smaller AC include the step of introducing suction to the AC and waiting a period of time (typically 90 seconds) to allow the clot to potentially align with the AC and/or deform to engage with the distal tip of the AC. However, as shown in FIG. 5B, the application of aspiration pressure P1 may cause the clot Y to deform around the AC thus preventing the clot from being aspirated and/or causing the clot to fragment.

As shown in FIG. 5C, there is a greater likelihood of alignment of the distal tip of the G2BA with the clot which in a number of situations will improve the likelihood of clot capture.

The G2BA, with its larger distal tip opening, and hence improved likelihood of being perpendicular to the vessel is more likely to be aligned and sealed against the vessel wall. Hence, the application of suction can be more effective in that there may be less "leakage" from around the distal tip.

Method to Prevent Clot Fragmentation/Emboli in New Territory

In other aspects, the invention provides a method to reduce clot fragmentation and/or a method to reduce emboli in new territory. As is known, clots may be comprised of different zones or segments having different compositions that affect the overall rigidity/cohesion of the clot. Generally, a blood clot may range in composition and consistency between tougher fibrin-rich zones/fragments and softer zones/fragments where the cohesion between these zones may be relatively strong or relatively weak. Fibrin-rich zones will generally have greater cohesive forces that hold the clot together whereas other zones may be less cohesive and be more susceptible to fragmentation. It is a common occurrence when using smaller aspiration catheters and/or when the clot is fibrin-rich that the clot will "cork" in the end of the catheter and cannot be withdrawn through aspiration into the catheter. If a clot is corked, it requires withdrawal of the AC which has two main potential downsides. Firstly, the act of withdrawing results in a loss of position which will require time to regain if necessary. Secondly, the act of withdrawing can cause a clot to fragment wherein only a part/fragment of the clot is withdrawn and leaves a portion/fragment of the clot at the clot site. This clot fragment may be smaller and go into distal vessels making retrieval even tougher. Also as the clot is being withdrawn, it comes across the origin of other big vessels. For example, when the catheter is being withdrawn from the MCA, it will cross the origin of ACA: at that time the clot may fragment and a part of the clot may go into the ACA resulting in a new stroke, commonly called: infarct in new territory (INT).

If fragmentation occurs, this then requires that after withdrawal of the first piece, the AC must be readvanced back to the clot face to remove the one or more remaining fragments which is a significant time delay to reperfusion.

As such, the G2BA also provides a method of reducing clot fragmentation by improving the aspiration forces being applied to a clot at the intended levels of the G2BA, which are more likely to fully ingest the clot which then reduces the likelihood of requiring G2BA withdrawal which can cause fragmentation.

Similarly, a clot that is not fully aspirated or withdrawn may fragment into one or more additional pieces/emboli that travel to distal sites. Thus, the G2BA also provides a method of reducing emboli in new territory by applying an improved aspiration pressure to a clot that increases the likelihood that any smaller fragments that would otherwise create distal emboli are aspirated together with the main fragments of the clot.

Oblique G2BA Tip and Torquable G2BA

FIG. 5A shows that the tip of an AC may be deflected as it pushed around a curve such that the distal tip may have an angle θ, with respect to the vessel wall. Depending on the particular orientation of the distal tip and the particular proximal surfaces of the clot, this contact angle between the distal tip and the clot may assist aspiration or alternatively negatively affect aspiration. For example, aspiration can be enhanced if the distal tip forms an elliptical opening and the distal tip is oriented in such a was so as to improve the contact angle with the clot; however, equally the contact angle between the distal tip and the clot may impair aspiration if the oblique surface is not "parallel" to the proximal surface of the clot. Generally, oblique surfaces can increase the surface area of contact further increasing the chance of the clot being ingested. In the past, aspiration catheters were not designed to be torquable and hence, be able to control or change the contact angle.

Current catheters are not torquable as they are made of soft material and torqueing (applying a rotational force) at the part of the catheter that is outside the body does not transmit the force to the distal end but instead damages the catheter itself.

Figure 5D:
FIG. 5D is a schematic diagram showing a G2BA catheter having an oblique tip that is torquable.

In one embodiment, the G2BA is constructed such that the proximal portion of approximately 100-120+ cm is torquable and hence, there is the only the distal 15-20+ cm of the softer distal portion where the torque force is transmitted resulting in a greater likelihood where the application of a torque force is successful in rotating the distal tip. FIG. 5D shows a G2BA 10 having a torquable distal portion with an oblique distal tip 10b that can be torqued to improve the contact angle between the oblique distal tip and the clot. Generally, in many cases, it would be desirable to ensure that the outer distal tip is placed on the outside of a curve and/or is positioned adjacent the most proximal edge of the clot. In order to enable visualize placement of the distal tip, a radio opaque marker 40 is placed in the visual tip.

In some cases, the physician may not fully know the position of the distal tip relative to the vessel and it will be rotational movement of the oblique tip under suction pressure that causes the most favorable orientation of the tip in the vessel and which causes sudden ingestion of the clot.

Further Distal Procedures

Figure 6A:
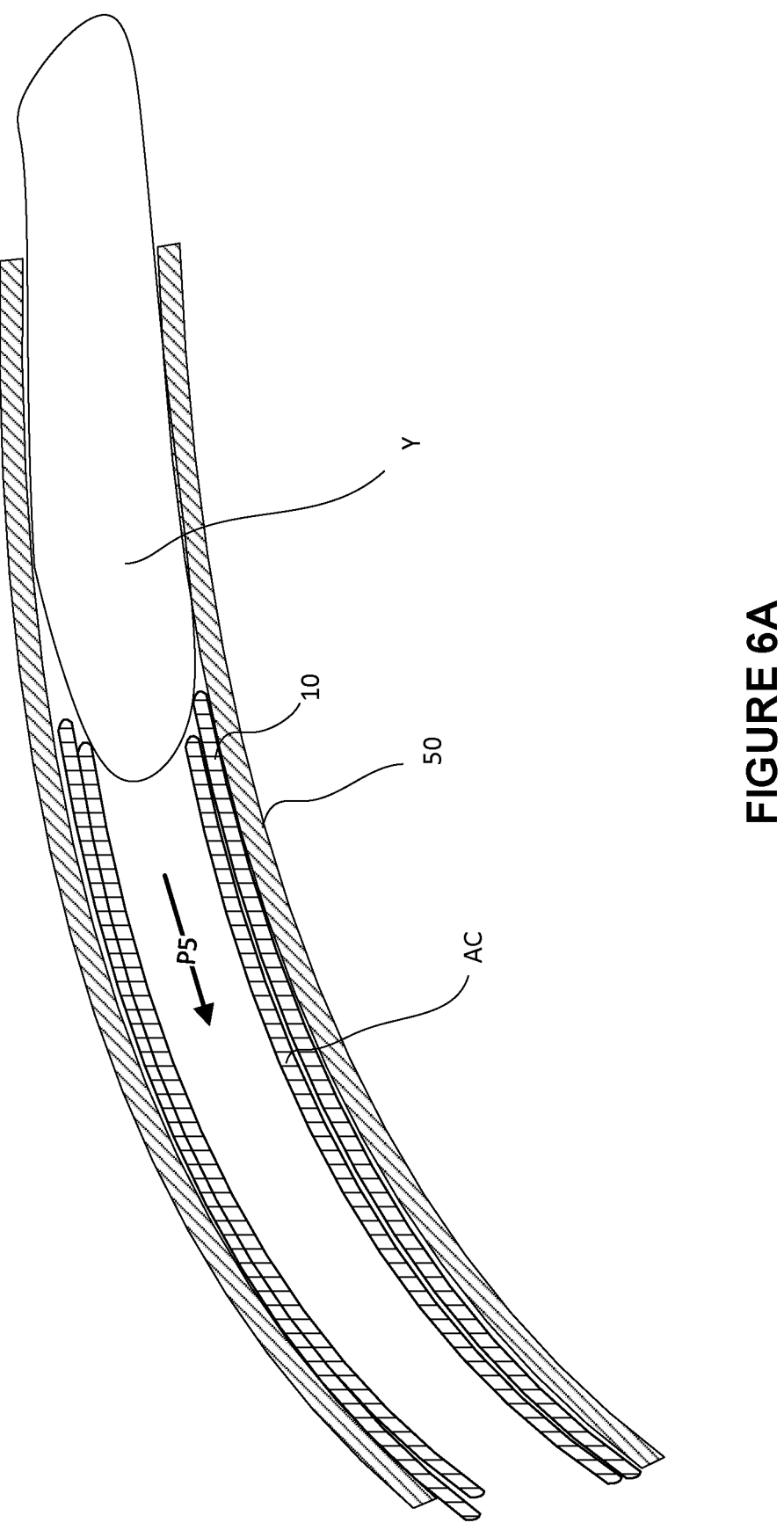
FIG. 6A is a schematic diagram showing a clot corked in a G2BA and an aspiration catheter proximal to the distal tip of the G2BA.

In other embodiments, methods of enhancing capture of a corked clot are described. In one example, after attempts to aspirate a clot have been made with a G2BA, the clot may have corked in the distal tip. The physician may choose to withdraw the G2BA and hope that the clot does not fragment and/or result in distal emboli which under either scenario would require losing position if the G2BA is withdrawn. As shown in FIG. 6A, one solution that the G2BA provides is the option to run a further aspiration catheter AC through the G2BA 10 such that it reaches the distal tip of the G2BA and the corked clot (while maintaining a negative/suction pressure through the smaller AC to hold the corked clot). In a typical G2BA deployment, the G2BA is an 8F catheter, thus enabling an approximately 6F AC to be run up the G2BA. Preferably, the 6F catheter is designed such that the catheter cannot protrude out of the G2BA and hence cannot accidentally dislodge the clot that is corked at the tip. Importantly, by placing the 6F AC on the corked clot as shown in FIG. 6A, a substantially larger suction force P5 can be applied through the 6F AC. Higher suction pressures in the center of the corked clot can enhance the ability to aspirate albeit into a smaller catheter. Even if it cannot be aspirated into the smaller catheter, the additional suction force would allow it to be held firmly at the tip and when the 6F catheter is withdrawn, it facilitates the process of the entire clot getting ingested by the bigger catheter. Thus, with the application of this additional suction pressure and withdrawing the 6F AC, may cause the corked clot to be eased into the 8F G2BA which can then be withdrawn all the way out within the G2BA or the entire assembly can be withdrawn. In one embodiment, if a clot gets stuck in a G2BA during suction, an AC can be advanced within the G2BA to apply suction pressure and potentially dislodge and/or assist in drawing the clot out without losing position.

In a further embodiment, after aspiration of a clot, standard procedure is to conduct a check angiogram to determine if the entirety of the clot has been removed. In some cases, fragments of the clot may have embolized and travelled distally that will be detected by the check angiogram. In this case, a secondary distal procedure may be conducted.

Figure 6B:
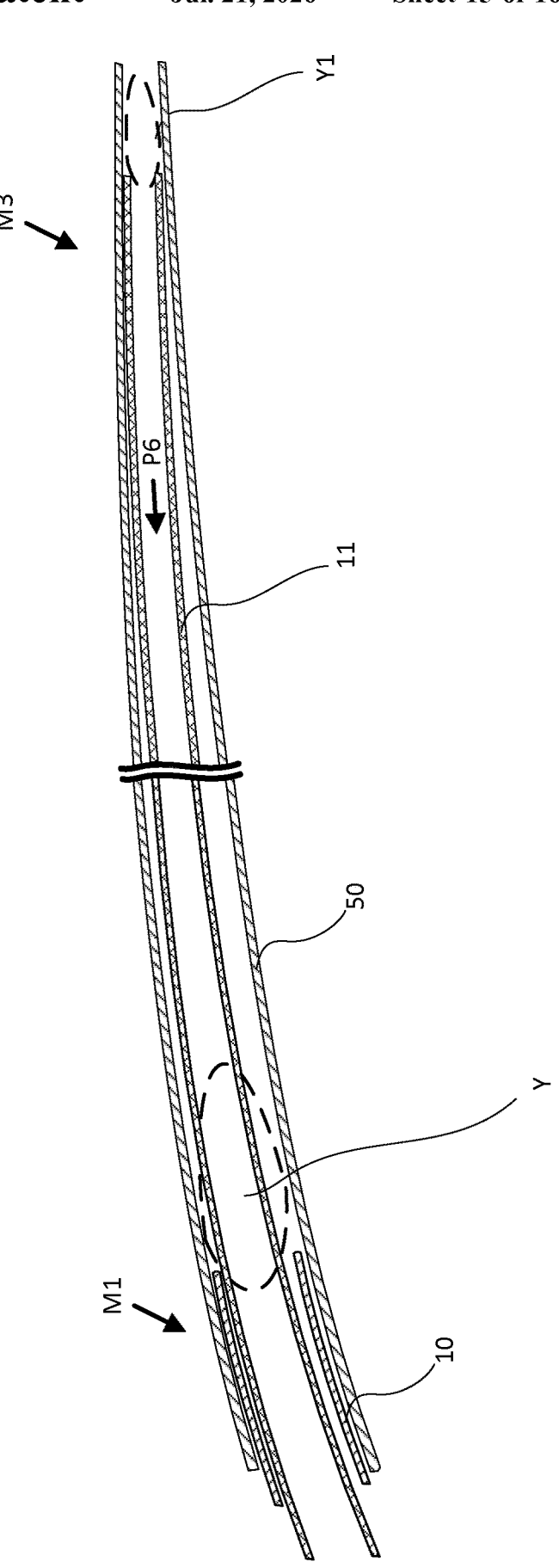
FIG. 6B is a schematic diagram showing a G2BA catheter and a second G2BA catheter being used to conduct a secondary aspiration of a distal emboli.

For example, as shown in FIGS. 3A and 6B, if when aspirating a clot Y through an 8F catheter 10 from the M1 segment, a check angiogram conducted with the G2BA in position determines that a smaller emboli Y1 has broken away and has lodged distally within an M3 segment, the physician may decide to conduct an alternate secondary distal procedure in which the following steps are followed:

a) While holding the first G2BA 10 in position, a second longer G2BA 11 (having an approximate 5F OD) is advanced through the first G2BA together with a second ISC (and second MW; 11a FIG. 3A). The second G2BA 11 is sized for co-axial movement within the first G2BA and is initially advanced to the distal tip of the first G2BA;

b) The second MW and second ISC are advanced beyond the distal tip of the first G2BA by selective manipulation of the second ISC, second MW and second G2BA until the proximal face of the emboli Y1 is reached;

c) The second ISC and second MW are removed;

d) Suction P6 is applied to the second G2BA through a pump to aspirate the emboli into the second G2BA. If aspiration is not successful but there is no blood coming back, the clot has likely engaged with the distal tip but won't aspirate into the second G2BA. In this case, the second G2BA can be withdrawn (with the engaged clot fragment Y1) into the first G2BA and the second G2BA withdrawn through the first G2BA.

e) A check angiogram is conducted;

f) If clear, the first G2BA (and second G2BA if still in place) is/are removed.

g) If not clear, further options may be evaluated.

The G2BA may also be used in pediatric cases in which case appropriately smaller G2BA catheters would be utilized based on the relative height/size of the patient.

Underlying Stenosis

In another application, periodically there may be a requirement to stent an underlying stenosis at the same time as removing a clot. Stenting may be required due to tight stenosis in the carotid or intracranial vessels. As a stent is relatively stiff, it can be problematic to push these stents across all the curves and tortuousity of the vasculature. Also if the external diameter of the stent is bigger than the traditional aspiration catheter of guide sheath, these have to withdrawn to allow for a bigger system. Hence, there can be an advantage to utilizing a G2BA for these procedures. In this case, stents having longer push wires to enable them to travel through the G2BA are required. That is, current stents would require longer push wires to enable them to be deployed through the longer G2BA catheter.

Radial Artery Access

As noted, a DEP may be the radial artery. Accessing the cervical arteries from the radial artery requires travel through the radial artery, brachial artery to the aortic arch which typically requires a 180 degree turn of the DC/GW to hook the desired carotid artery. As such, once placed, the G2BA provides advantages over past AC/GC systems as the distal section of the G2BA can more readily ride over the GW/DC and make the sharp turn at the aortic arch.

Brain Cooling

It is known that cooling the brain has a neuroprotective effect when the brain has been deprived of oxygen. In the case of stroke, cooling the brain prior to or after removal of a clot has been considered. Cooling the patient's entire body is generally complicated in that the effects of shivering will typically require general anesthetic and/or muscle relaxants. As a result, attempts have been made to effect cooling by direct cooling of the brain by introducing cooled fluids through catheters into the brain after a clot has been removed using the same catheter systems. However, introducing cold fluids (typically cold saline) directly into the brain through catheters has not been successful as the cold fluids cannot be adequately insulated from the warm body from the point of introduction while they travel to the brain. For example, a 6F catheter used as an aspiration catheter does not provide sufficient insulation to directly convey a cooling fluid to the brain and, hence requires further insulation if it is to be effective. However, a 6F catheter can only convey an approximate 4F catheter having a 2F lumen for carrying cooling fluids. Given the length of a typical aspiration catheter, by the time cold fluids (eg. Introduced at approximately 1 C) have travelled the length of the catheter, there is still insufficient insulation for there to be an effective cooling effect. That is, upon exit from the catheter injected fluids may exit the catheter at 15 C or greater which is insufficient to provide effective cooling. Furthermore, the problem cannot be solved by introducing a larger volume of fluid as there is a limit to the volume of fluids that can be introduced as increased fluid volumes can cause other effects including pulmonary edema.

In addition, adding insulation to the catheter wall changes its properties and makes it stiffer. Such an insulated catheter is generally not able to negotiate past the various curves to get to the brain vessels when being pushed through a 6F catheter. Also since the insulation takes space, the inner lumen is quite small and as such does not allow space for an ISC to facilitate getting past curves.

There have been attempts to design catheters where the distal 15 cm is thinner and without insulation while the proximal part is insulated to overcome the stiffness problem. However, even then there is substantial loss of cooling efficiency due to heating of the cold saline in the last 15 cm. However, with a larger G2BA catheter in the brain, the volume available to insulate is increased. In addition the insulation can be carried all the way to the tip of the cooling catheter as the cooling catheter has a greater volume to travel within which allows flexibility to be incorporated into the distal portion as well as increased insulation. For example, after an 8F G2BA catheter has been positioned in the M1 segment of the MCA and used to aspirate the clot, an insulated 6 F catheter with a larger and insulated wall is inserted into the G2BA and run to the distal tip of the G2BA. With greater insulation, fluids introduced at 1-3° C. may exit at a temperature of 2-8° C. which is sufficient to be effective for brain cooling.

Figure 6C:
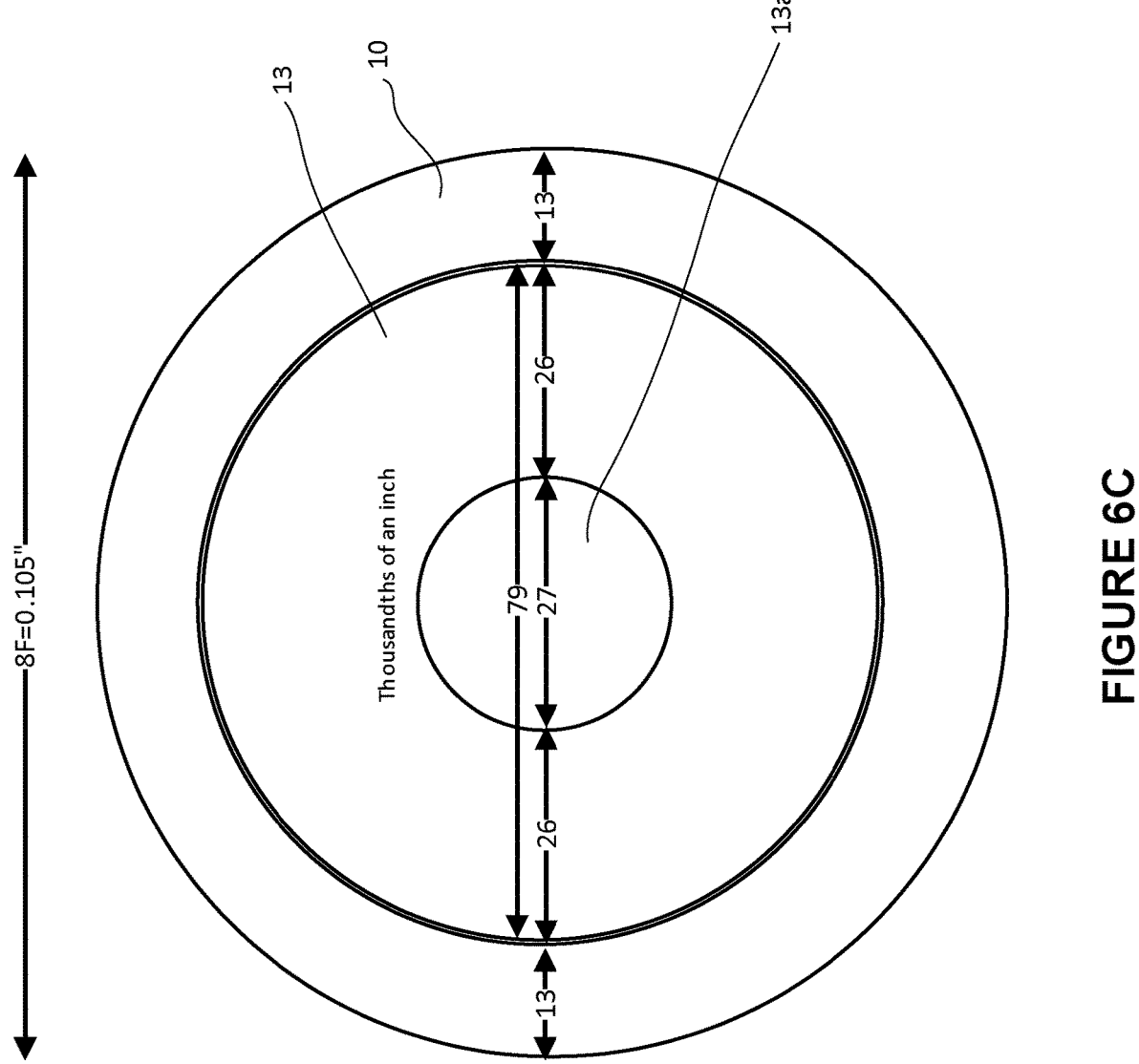
FIG. 6C is schematic diagram of an insulated/cooling catheter within a G2BA catheter.

The insulated catheter is substantially the same length (nominally longer) as the G2BA catheter and sized to fit within the G2BA. As shown schematically in FIG. 6C, an 8F G2BA 10 will have an OD of 0.105" and a typical wall thickness of 0.013" allowing a 6F insulated catheter 13 to travel within. The insulated catheter will have an OD of 0.079" and may have a wall thickness in the range 0.026" thus having a lumen of 0.027". The thicker walls provide additional insulation sufficient to convey cold fluids to the distal tip of the G2BA and into the cerebral circulation. A lumen size of 1.5F is the approximate minimum lumen size for conveying a sufficient volume of fluid.

In one embodiment, a fluid cooling module is utilized to deliver cooling liquid to the proximal end of a cooling catheter. Generally, the fluid cooling module includes a fluid pump and controller for pumping a calculated volume of cooling liquid through the cooling catheter. The calculated volume is determined based on modelling of heat transfer through the cooling catheter, modelled data of a D2BA catheter as selected for a patient, patient data and a desired cooling liquid temperature at a distal end of the cooling catheter.

In one embodiment, an ISC is also used as a cooling catheter referred to an integrated support and cooling catheter (ISCC). In this case, an ISCC having proximal insulation would be used to advance the G2BA catheter. Once the ISCC has been withdrawn and the aspiration procedure taken place, the ISCC would be re-introduced and cooling solution flow introduced. As with an ISC, the ISCC includes a tapered distal zone for supporting the distal tip of the G2BA during advancement through tortuous sections of a patient's cerebral vasculature and an insulated proximal zone enabling a cooling solution to introduced to a proximal end of the ISCC. From a performance perspective, cooling fluid introduced at the proximal end at 1-3° C. would exit the ISCC at 2-8° C.

Suction and Suction Pulses

Other procedures and devices may be employed to improve suction efficiency once a G2BA is in position.

The application of suction pulses can also be used to improve engagement of the G2BA with the clot. As a tighter seal with the vessel wall is likely higher, a short pressure pulse or pulses may cause the G2BA or the clot to move closer to the other and cause a more rapid engagement and/or ingestion, thus obviating the need to wait a time period for the catheter and clot to engage. For example, application of 1-3 short lower pressure pulses followed by a larger pressure pulse can successively align or partially ingest the clot followed by a higher pressure pulse(s) that fully ingests the clot.

Further still, measurement of the pressure wave at the pump can be utilized to quantify the effectiveness of the aspiration process by a comparison of the applied pressure wave vs. a response measured at the pump. Analysis of the response can be used to dynamically adjust a delivered pressure. That is, a pressure wave may be generated by the pump and a measure of the pressure/flow waveform received back from the G2BA can be compared to determine the effectiveness of the aspiration pressure in seating the G2BA against the clot and/or aspiration of the clot.

The pressure wave can also compensate for the compliance of the G2BA.

In a further embodiment, aspiration pumps could be wifi enabled thus capturing suction pulse data and using that data through machine learning and artificial intelligence based algorithms to improve the pressure pulse and using the information gained from the first pressure pulse to improve the next pressure pulse based on the A1 algorithms developed from the continuously growing database of past performance.

Further, the suction pressure on the aspiration pump may be higher given the increased diameter of the G2BA.

Preferably, the aspiration pump will include a filter that will capture any aspirated clot. Visual inspection of a clot at the aspiration pump together with or separate to flow rate data through the G2BA can provide effective information as to whether or not circulation has been established and the procedure has been successful.

Pulse pressure algorithms may also be applied to the further distal procedures described above.

G2BA Kits

Various kits may be provided in accordance as summarized in Table 5 where kits are assembled based on a target level (referred to here as Levels 1-4 where level 1 is deeper (eg. level 2 segments) and level 4 is lower in the vasculature.

TABLE 5

| G2BA/DC and ISC Kits | | | |
|---|---|---|---|
| Target Level | G2BA | DC/MW | ISC |
| 1 | FR 7 | A | FR 6 |
| 2 | FR 8 | A | FR 7 |
| 3 | FR 9 | A | FR 8 |
| 4 | FR 10 | A | FR 9 |
| 1 | FR 7 | B | FR 6 |
| 2 | FR 8 | B | FR 7 |
| 3 | FR 9 | B | FR 8 |
| 4 | FR 10 | B | FR 9 |
| 1 | FR 7 | C | FR 6 |
| 2 | FR 8 | C | FR 7 |
| 3 | FR 9 | C | FR 8 |
| 4 | FR 10 | C | FR 9 |
| 1 | FR 7 | A, B, C | FR 6 |
| 2 | FR 8 | A, B, C | FR 7 |
| 3 | FR 9 | A, B, C | FR 8 |
| 4 | FR 10 | A, B, C | FR 9 |

Generally, a surgeon will select a kit based on the target level and an understanding of the vessel diameter at the clot. In addition, kits may be provided with specific DC/GW combinations selected on the basis of a surgeon's diagnostic assessment of a patient's aortic arch. Table 5 refers to DCs by generic placeholders A, B, C with each DC having particular tip/stiffness/shape characteristics.

As the cost difference between DCs vs. ISCs and G2BAs may be significant, kits may include multiple DCs.

Still further kits are described:
a) Kit containing $2^{nd}$ G2BA, ISC and MW of appropriate diameters for use in conjunction with or included in kits shown in Table 5 for conducting secondary distal procedures.
b) Kits shown in Table 5 with an additional AC sized to fit within a G2BA. The AC would have a length that would prevent it from emerging from the distal tip of the G2BA
c) Any Kit described above together with a cooling catheter.

SUMMARY OF ADVANTAGES

The following advantages are realized by use of the G2BA and G2BA deployment methods together with an ISC in particular.
a) Fewer catheters (importantly no GC or BGC).
b) Fewer steps and faster.
c) Bigger catheter further.
d) Ability to advance through difficult sections.
e) Better tip alignment when suction is applied.
f) Reduced likelihood of introducing bubbles into the circulation as fewer catheters are utilized that may have been inadequately flushed.
g) Reduce the need for larger groin sheaths.
h) Reducing procedure costs especially by potentially obviating the need for a stent-retriever.
i) Increasing the reperfusion rates thereby improving patient outcome.
j) Reducing possible delays in the OR that have been caused by coronavirus by reducing equipment being passed from personnel to personnel.
k) Improving the speed of procedures conducted using stiffer DCs by providing a softer G2BA distal zone that can ride over a stiffer DC. This may encourage a surgeon to choose DCs better suited for engaging the origin of the appropriate cervical artery.

l) Decreasing the likelihood of clot fragmentation by allowing complete ingestion of the clot.

m) Improving the overall ability to suck a non-heterogeneous clot. Some clots have different consistencies and may fragment between regions having the different consistencies. By having a suction catheter that is close in size to the clot (and the vessel), the likelihood of clot ingestion is much higher. By enabling stronger pulse pressures to be applied with an improved likelihood of sealing against the entire clot, both fibrous and non-fibrous clots may be more effectively ingested.

n) Improving speed to access secondary distal emboli with a secondary G2BA and ISO and remove a distal emboli.

o) Decreasing likelihood of causing secondary distal emboli.

p) Improving access from radial artery.

q) Providing easier access of a stiff stent system in case of significant intracranial or carotid atherosclerotic disease.

r) Providing easier access for an insulated catheter to deliver cold solutions for local hypothermia if the ischemic territory.

From the foregoing, it is important to note that the structural and functional properties of a D2BA catheter are distinguished over the properties of other catheters. That is, while catheters enabling aspiration functions to be performed and catheters having a range of physical sizes and stiffnesses appear similar, the differences in sizes, lengths and performance characteristics in combination are significant in that the combination of physical and functional properties enable new procedures to be conducted that have real-world benefits to patients. Moreover, as a wide range of manufacturing techniques and materials can be combined in different ways to provide catheters having the unique combination of physical and functional properties, emphasis is made on the understanding of the need to balance specific mechanical and chemical properties of the materials that may be used in catheter construction to provide the desired end functional capabilities.

The invention claimed is:

1. An endovascular method for gaining access to cervical and cerebral arteries, the endovascular method for placing a catheter system within a human vasculature between a distal entry point (DEP) and cerebral arteries and aspirating a cerebral clot in one of the cerebral arteries, the method comprising the steps of:

a) introducing a catheter system including a D2BA catheter, guide wire (GW) and diagnostic catheter (DC) through a DEP;

b) advancing the catheter system to an aortic arch;

c) advancing the GW and DC to a desired cervical artery and manipulating the GW into a desired cervical artery;

d) advancing the D2BA catheter to a desired carotid artery over the DC and GW;

e) removing the DC and GW;

f) introducing an internal support catheter (ISC) having a tapered distal section for supporting a distal end of the D2BA catheter and adapted to facilitate movement of the distal end through tight curves in the cerebral vasculature and an ISC microwire (ISC MW);

g) advancing the ISC and ISC MW to the cerebral artery with the clot;

h) advancing the D2BA catheter to a proximal face of the clot and withdrawing the ISC and ISC MW; and, i) applying suction to the clot through the D2BA catheter;

j) comparing a pre-determined pressure pulse against a measured response pressure at a suction pump and adjusting subsequent pressure pulses based on the measured response pressure;

where step i includes applying one or more first pressure pulses through the D2BA catheter to assist in engaging a distal tip of the D2BA catheter against the clot followed by at least one second aspiration pulse to aspirate the clot;

wherein the step of adjusting subsequent pressure pulses considers pressure response data from a plurality of patients collected and analysed from similar procedures;

wherein suction is applied via a suction pump operatively connected to the internet and a central computer system and wherein pressure response data from different pumps is received and analysed by the central computer system and wherein pump pressure algorithms are updated via the internet to the different pumps.

2. The method as in claim 1 further comprising the steps of:

k) after applying suction to withdraw a clot in step i, conducting a check angiogram to determine if the entire clot has been withdrawn and if one or more distal emboli are present and if present:

l) advancing a second D2BA catheter sized for co-axial movement within the D2BA catheter together with a second ISC and second ISC MW to a proximal face of the distal emboli; and, m) applying suction to the second D2BA catheter to withdraw the distal emboli via aspiration or by withdrawing the second D2BA catheter.

3. The method as in claim 1 where step i includes applying one or more first pressure pulses through the D2BA catheter to assist in engaging a distal tip of the D2BA catheter against the clot followed by at least one second aspiration pulse to aspirate the clot.

4. The method as in claim 3 wherein pump pressure algorithms consider catheter materials, brand and/or size.

5. The method as in claim 1 wherein if aspiration has been unsuccessful further comprising the step of introducing a cooling catheter into the D2BA catheter and advancing the cooling catheter to the distal tip of the D2BA catheter and flushing a cooling solution through the cooling catheter to affect cooling of brain tissue.

6. The method as in claim 5 further comprising the step of flushing the cooling solution through the cooling catheter.

7. The method as in claim 6 wherein the cooling catheter further having proximal insulation and where after the ISC has been withdrawn and aspiration has been completed, the ISC is re-introduced and cooling solution is flushed through the ISC.

8. A method for gaining access to cervical and cerebral arteries, comprising:

advancing a catheter system to an aortic arch, the catheter system comprising an aspiration catheter, a guide wire, and a diagnostic catheter;

advancing the guide wire and the diagnostic catheter to a desired cervical artery;

advancing the aspiration catheter to a desired carotid artery over the diagnostic catheter and the guide wire;

removing the diagnostic catheter and the guide wire;

advancing an integrated support and cooling catheter to a clot within a cerebral artery, the integrated support and cooling catheter comprising a cooling lumen and a tapered distal section;

advancing the aspiration catheter to the clot and withdrawing the integrated support and cooling catheter;

aspirating the clot with the aspiration catheter;

reintroducing the integrated support and cooling catheter to a previous location of the clot after the clot has been aspirated;

cooling the previous location of the clot by flushing a cooling solution through the integrated support and cooling catheter.

9. The method of claim 8, wherein the integrated support and cooling catheter comprises a length greater than the aspiration catheter.

10. The method of claim 8, further comprising the step of introducing an integrated support and cooling catheter microwire.

11. The method of claim 10, further comprising advancing the integrated support and cooling catheter microwire to the cerebral artery with the integrated support and cooling catheter.

12. The method of claim 8, further comprising applying a first pressure pulse through the aspiration catheter to assist in engaging a distal tip of the aspiration catheter against the clot.

\* \* \* \* \*